(12) United States Patent
Rehg et al.

(10) Patent No.: US 6,194,221 B1
(45) Date of Patent: Feb. 27, 2001

(54) HYBRID ONE-STEP IMMUNOCHROMATOGRAPHIC DEVICE AND METHOD OF USE

(75) Inventors: Leslie Rehg, San Diego; Ching Huang, Chula Vista; Michael J. Willrodt, Escondido; Herbert Bradfield Cunningham, Julian; Eugene Fan, La Jolla, all of CA (US)

(73) Assignee: Wyntek Diagnostics, Inc., San Diego, CA (US)

( * ) Notice: Subject to any disclaimer, the term of this patent is extended or adjusted under 35 U.S.C. 154(b) by 0 days.

(21) Appl. No.: 08/963,412

(22) Filed: Nov. 3, 1997

Related U.S. Application Data

(63) Continuation-in-part of application No. 08/752,695, filed on Nov. 19, 1996, now abandoned, and a continuation-in-part of application No. 08/900,559, filed on Jul. 25, 1997.

(51) Int. Cl.[7] .................................................. G01N 33/533
(52) U.S. Cl. ............................ 436/514; 422/55; 422/56; 422/57; 422/58; 422/59; 422/61; 435/7.1; 435/7.34; 435/7.92; 435/7.95; 435/287.7; 435/287.9; 435/885; 435/969; 435/970; 436/518; 436/528; 436/530; 436/541
(58) Field of Search ............... 422/55–61; 435/7.1–7.34, 435/7.92–7.95, 287.7–287.9, 885, 969, 970, 514; 436/518, 528, 530, 541

(56) References Cited

FOREIGN PATENT DOCUMENTS

2204398 * 11/1988 (GB).
9633413 * 10/1996 (WO).

OTHER PUBLICATIONS

Osom Steep A Test, Package Inserts, Wyntek Diag.1996.*

* cited by examiner

Primary Examiner—Christopher L. Chin
Assistant Examiner—Bao-Thuy L. Nguyen

(57) ABSTRACT

This invention relates to a lateral flow immunochromatographic assay device with an increased range of sensitivity without an increase in the clearance time or the occurrence of false positive results. The indicator reagent for the analyte is located in both a separate labeling reagent region and a discrete zone of the analyte detection region.

15 Claims, 10 Drawing Sheets

HYBRID ONE-STEP IMMUNOCHROMATOGRAPHIC DEVICE AND METHOD OF USE

RELATED APPLICATION

This application is a continuation-in-part to Cunningham, Huang, Rehg, Fan and Willrodt, ONE-STEP IMMUNOCHROMATOGRAPHIC DEVICE AND METHOD OF USE, Ser. No. 08/752,695, filed on Nov. 19, 1996 now abandoned and a continuation-in-part to Cheng, Wu, Cunningham, Huang, Fan and Willrodt, METHODS OF USE OF ONE STEP IMMUNOCHROMATOGRAPHIC DEVICE FOR STREPTOCOCCUS A ANTIGEN, application Ser. No. 08/900,559, filed on Jul. 25, 1997, now pending incorporated herein by reference including drawings.

BACKGROUND OF THE INVENTION

This invention relates to immunological methods and devices for detecting analytes in biological samples.

Numerous approaches have been developed for detection of a given analyte in a biological sample. Typical of these methods are the so called "lateral flow" and "flow-through" devices and methods. The flow-through device generally uses a porous material with a reagent-containing matrix layered thereon or incorporated therein. Test sample is applied to and flows through the porous material, and analyte in the sample reacts with the reagent(s) to produce a detectable signal on the porous material. These devices are generally encased in a plastic housing or casing with calibrations to aid in the detection of the particular analyte.

Lateral flow assays also utilize a porous membrane for performing analyte detection. Instead of drawing the sample through the membrane perpendicularly, the sample is permitted to flow laterally from an application zone to a reaction zone on the membrane surface. The capture reagent is present in the reaction zone, and the captured analyte can be detected by a variety of protocols, including direct visualization of visible moieties associated with the captured analyte.

One-step lateral flow assays permit a user to add a sample to a sample application region and obtain a positive or negative signal signaling the presence or absence of the test analyte in the sample.

One-step lateral flow devices contain a sample application region to which the sample is applied. The sample application region is in lateral flow contact with the porous carrier material of the analyte detection region. During lateral flow, the sample is brought into contact with a mobile indicator reagent in a discrete zone of the analyte detection region. The indicator reagent contains both a binding moiety which specifically binds to the target analyte and an indicator moiety, which is most often a chromophore label. Target analyte molecules moving in the lateral flow bind to the indicator reagent and are ultimately immobilized in the capture zone, usually by binding to a second reagent which binds specifically to the analyte or to the analyte-indicator reagent complex. The position of the immobilized indicator reagent gives rise to a positive signal. Additional signals may include a negative reaction indicator, a test complete indicator, and a positive control indicator.

One-step immunochromatographic devices containing the indicator reagent in a discrete zone of the lateral flow porous material, e.g., at a discrete site on the test strip, have been described.

For example, Deutsch et al. describe a quantitative chromatographic test strip device in U.S. Pat. Nos. 4,094,647, 4,235,601 and 4,361,537. The device comprises a strip of material capable of transporting a solution by capillary action, i.e., wicking. Different areas or zones in the strip contain the reagents needed to produce a detectable signal as the analyte is transported to or through such zones. A diffusible label which can bind to the test analyte may be located in a discrete region of the strip. The device is suited for both chemical assays and binding assays which are typified by the binding reaction between an antigen and its complementary antibody.

In addition, British Application No. 2,204,398 describes a lateral flow device wherein sample applied to the device picks up labeled reagent located at a discrete site on the porous carrier of the strip and permeates into a detection zone. The indicator labels include gold sols and colored particles.

Alternatively, devices containing the mobile indicator reagent in a separate porous material or pad have been disclosed.

For instance, European Publication No. 323,605 discloses an assay device using chromatographic material wherein the test sample can travel from one end to the other by capillary action. The chromatographic material contains an immobilized capture reagent capable of binding to the analyte. The application pad which receives the test sample also contains a diffusible indicator reagent capable of migrating from the application pad to the chromatographic material. The indicator reagent is capable of binding to the analyte. The binding of the indicator reagent-analyte complex results in a detectable signal at the capture situs.

PCT application No. WO 94/06013 also describes a lateral flow assay in which the indicator reagent has been placed in a separate indicator reagent region or pad (referred to as "the third liquid permeable material"). The sample is added to a separate sample application pad, passes through a second permeable material, and mobilizes the indicator reagent located in the third liquid permeable material. The sample then enters the wicking material containing the capture zone.

Patent application Wo 92/01226 describes a lateral flow device in which the labeled specific binding reagent is retained in the dry state either in a zone on the carrier material Ao in a separate porous body through which the sample passes en route to the porous carrier material of the test strip.

U.S. patent application Ser. No.08/444,238 and its corresponding PCT application 99/04748 also describe lateral flow assay devices in which the labeled reagent for the analyte is located in a discrete zone of the porous carrier material of the analyte detection region.

Other variations of test strip assays are disclosed in U.S. Pat. Nos. 4,298,688, 4,517,288 and 4,740,468, which describe sheet-like diagnostic devices comprising one or several strips, arranged behind one another, having zones situated one behind another. Each zone is readily accessible from above and below for the addition of reagents. Such devices can quantitatively determine the amount of an analyte.

Procedures using chromogenic and fluorescent dyes as labels in biological assay procedures are also known. Typical assay protocols call for direct or indirect binding of a dye label to an analyte or analyte analog in a biological sample, where the presence or absence of the dye at a particular stage of the assay can be determined visually and related to the amount of analyte initially present in the sample. A wide variety of specific assay protocols exist.

A number of those assays utilize naturally colored or dyed particles as a label, where the particles are bound to an antibody or other specific binding substance. Suggested particles include dyed latex beads, dye imbibed liposomes, erythrocytes, metal sols, and the like. The colored particle in such complexes can serve as a visible marker, where separation, capture, or aggregation of the particles is mediated through binding of the antibody or other specific binding substance. The amount of label thus segregated in a particular assay step is related to the amount of analyte initially present in the sample.

For example, U.S. Pat. No. 4,943,522 describes a solid phase lateral flow assay using erythrocytes as a label. U.S. Pat. No. 4,863,875 describes compositions comprising at least ten dye molecules or monomers covalently attached to an antibody through an isocyanate group on the dye. U.S. Pat. No. 4,703,017 describes a solid phase assay device which relies on specific binding of a ligand-label conjugate on a solid support, where the label is disclosed as a particle, such as a liposome, or polymer microcapsule. U.S. Pat. No. 4,608,246 describes assays for typing blood which employ erythrocytes as a labeling agent. U.S. Pat. No. 20 4,452,886 describes the covalent attachment of photon absorbing or emitting polymers to proteins, such as antibodies and antigens. U.S. Pat. No. 4,373,932 describes labeling of a ligand with an aqueous dispersion of a hydrophobic dye or pigment, or a polymer nuclei coated with such a dye or pigment. U.S. Pat. No. 4,313,734 describes methods of detecting sample analytes by the determination of the metallic label content in the sample. U.S. Pat. No. 4,169,138 describes immunoassays which employ visible particles including undyed microorganisms, bound to polymers which may be of microbial origin.

Other lateral flow protocols include U.S. Pat. No. 4,943,522 directed to a lateral flow device which relies on a nonbibulous support to conduct liquids from one portion of the device to another. PCT Publication WO 92/12428, which is related to the above patent, represents an improvemetnt on that method and device wherein nonbibulous lateral flow is used to conduct visible moieties, especially labeled particles, e.g., dyed latex, red blood cells or liposomes capable of reacting with analyte or a competitor thereto into a capture zone for detection, using a bibulous support made nonbibulous by treatment with a blocking agent. The result is a one-step assay which can be conducted in a very short period of time (typically, within 60 seconds), and wherein the readout is usually available instantaneously upon the sample contacting a capture zone.

These one-step assays are complex devices containing a number of immunoassay reagents. Because the ability to manipulate the sample is restricted, it is desirable to develop other design variations that increase the range of sensitivity of the assay without increasing either the time necessary to perform the assay or the number of false positive results.

None of the references described herein is admitted to be prior art.

SUMMARY OF THE INVENTION

This invention relates to an immunoassay device with an increased range of assay sensitivity. Changes in the concentration of labeling reagents, buffer composition of the labeling reagents, and arrangement of the labeling reagents can alter the sensitivity of the assay, the occurrence of false positive reactions, and the time required to obtain clearance of unbound indicator labeling reagents through the device.

The immunoassay devices of this invention increase the range of assay sensitivity without increasing the time needed to perform the assay or the occurrence of false positive reactions. The increased range of assay sensitivity is accomplished by providing at least two indicator labeling reagents which have different lateral flow characteristics.

The lateral flow characteristics of a given indicator labeling reagent may be altered, for example, by placing the indicator labeling reagent in two regions of the lateral flow device which have different lateral flow rates, or by altering the composition of the indicator labeling reagent solution applied to the lateral flow device. In addition, both the location and the composition of the two solutions containing the indicator labeling reagent may be altered.

Preferably the device contains two indicator labeling reagents differing in their lateral flow properties, i.e., a first indicator labeling reagent and a second indicator labeling reagent. Although the labeling reagents are designated as the first, second, ... nth indicator labeling reagents to denote the different lateral flow properties of the first through nth indicator labeling reagent, the actual analyte binding molecule of the indicator labeling reagents may be the same or different, as long as the lateral flow properties of the indicator labeling reagents differ.

For instance, the lateral flow properties of a given indicator labeling reagent may be altered by placing an indicator labeling reagent for the analyte in two distinct areas of the device—both in a discrete zone of the lateral flow porous carrier material of the analyte detection region, and in a separate porous region through which the sample must flow to the capture zone. In this example the indicator labeling reagent in the discrete zone of the lateral flow porous carrier may be termed the first indicator labeling reagent, while the indicator labeling reagent located in the separate porous zone may be designated as the second indicator labeling reagent, or vice versa.

Alternatively, or in addition, two solutions containing an indicator labeling reagent may be applied to different zones of the device. The composition of the indicator labeling solution may be altered, for example, by altering the concentration of solutes in the solution. Different solutions of indicator labeling reagent containing different concentration of solutes can be applied to different zones of the device and then dried, resulting in changes in the viscosity of the sample as it passes through these different zones of the device, or changes in the rehydration rate of the indicator labeling reagent. The differences in the viscosity of the sample solution as it laterally flows through these zones, or in the rehydration rate of the indicator labeling reagent, will impart different lateral flow properties as the sample flows through these two zones. These zones may be on the same porous region of the device, or on separate porous regions.

Previously described one-step devices contained the indicator labeling reagent for the analyte in only one of two locations—either in the lateral flow porous carrier material of the test strip or in a separate porous material, for example, a pad of porous material. Moreover, previously described devices did not contain two or more different zones of indicator labeling reagents containing different compositions of dried solutes.

One-step devices which contain the indicator labeling reagent located in a discrete region in the lateral flow porous material, e.g., in a label zone on the test strip, have the advantage that the indicator labeling reagent is rehydrated, or mobilized quickly, leading to a quicker clearance time. That is, the time that it takes for unbound indicator labeling reagent to pass through the capture zone is shorter. However, because the analyte indicator labeling reagent complex has less time to incubate with and bind to the indicator capture reagent in the capture zone, and because the time for the indicator labeling reagent to bind to the analyte is shorter, these types of devices have a lower range of sensitivity than devices containing the indicator reagent in a separate labeling reagent region, or labeling pad. Moreover, increasing the level of indicator labeling reagent contained in the porous carrier in order to increase sensitivity increases the maximum concentration of indicator labeling reagent passing through the capture zone, which increases the possible number of false positive results.

On the other hand, placement of the indicator labeling reagent in a separate region, e.g., a porous pad, permits a more sustained release of indicator labeling reagent over a longer period of time. This results in a longer time period for incubation of the indicator labeling reagent with the analyte and a longer time period for movement of both bound and unbound indicator labeling reagent to pass the capture zone. This in turn gives rise to greater sensitivity, but also results in slower clearance times. Increasing the amount of indicator labeling reagent in the separate pad can further increase the low-end sensitivity, i.e., increase the ability to detect low concentrations of analyte, but results in even greater clearance times.

Thus, rather than increase the amount of indicator labeling reagent in either a separate porous indicator labeling reagent region, or in a discrete zone of the material of the lateral flow porous carrier of the analyte detection region, the devices of this invention contain at least two zones of indicator labeling reagent having different lateral flow properties. Thus, in one aspect, this invention describes an immunochromatographic assay device for detection of the presence or absence of an analyte in a liquid sample, where the immunochromatographic assay device comprises:

(a) a sample receiving region comprising a porous material which conducts lateral flow of a liquid sample, in lateral flow contact with (b) an analyte detection region comprising a porous material which conducts lateral flow of said liquid sample, wherein said analyte detection region comprises an immobile indicator capture reagent at a discrete indicator capture reagent situs, wherein said immunochromatographic device also comprises:

a first indicator labeling reagent zone comprising a first mobile indicator labeling reagent, and a second indicator labeling reagent zone comprising a second mobile indicator labeling reagent wherein the lateral flow characteristics of the indicator labeling reagent in the first zone differ from the lateral flow characteristics of the indicator labeling reagent in the second zone, and wherein said zones are in lateral flow contact with said sample receiving region and said analyte detection region, and wherein the liquid sample laterally flows from the sample receiving region towards the analyte detection region, and mixes with the first and second indicator labeling reagents to move the first and second indicator labeling reagents towards the analyte detection region.

In a first preferred embodiment, the devices of this invention contain indicator labeling reagent in both a separate porous material and located in a discrete region of the lateral flow porous carrier of the analyte detection region. This results in an increased range of sensitivity without giving rise to an increase in the number of false positives, or increasing the clearance time.

Thus, in a first preferred embodiment, the immunoassay devices of this invention may contain a first area of placement of the indicator labeling reagent in a separate porous material, e.g., a pad, which is contiguous with the sample receiving region and in direct contact with the lateral flow porous material of the analyte detection region (FIG. 1). The second area of placement of the indicator labeling reagent is in a discrete zone in the porous material of the analyte detection region. (FIG. 1). The indicator labeling reagent in the discrete zone is quickly mobilized when contacted by the lateral flowing sample fluid, thereby creating an initial high concentration of indicator labeling reagent passing through the capture zone. In addition, the placement of indicator labeling reagent in the separate porous material, i.e., a separate labeling reagent region, allows for sustained release of indicator labeling reagent as sample fluid moves through the separate labeling reagent region into the lateral flow porous material region by capillary action. The sustained release of indicator labeling reagent for the analyte facilitates low-end assay sensitivity by increasing the time of incubation of the indicator labeling reagent with the analyte, and increasing the time of incubation of the bound indicator labeling reagent with the indicator capture reagent in the capture zone. This results in an increase in the amount of bound label to pass through the capture zone without increasing the maximum concentration of label to pass through the capture zone (and the number of false positive results) and without increasing the clearance time compared to an assay device in which the indicator labeling reagent is placed only in a separate labeling reagent region.

In a second preferred embodiment the device contains at least two zones to which different indicator labeling reagent solutions have been applied. The different indicator labeling reagent solutions differ in the concentration of solutes. The indicator labeling reagent in the two solutions may bind to the same or different epitope of the analyte. If a solution of indicator labeling reagent is applied to the device in a solution having a low solute concentration, i.e., a low concentration of sugars such as sucrose, the indicator labeling reagent will be mobilized quickly, leading to a quicker clearance time but a shorter time for interaction of the indicator labeling reagent with the analyte.

On the other hand, if the indicator labeling reagent is applied to the device in a solution having a high solute concentration, the indicator labeling reagent will be mobilized more slowly, leading to a slower clearance time but greater sensitivity due to greater time for the indicator labeling reagent to incubate and bind to the analyte.

Thus, in a second preferred embodiment, the immunoassay devices of this invention may contain a first zone containing indicator labeling reagent which has been applied in a solution containing a low solute concentration. The second area of placement contains indicator labeling reagent which has been applied in a solution containing a high solute concentration.

The indicator reagent in the low solute zone is quickly rehydrated, or mobilized when contacted by the lateral flowing sample fluid, thereby creating an initial high concentration of indicator labeling reagent passing through the capture zone. In addition, the placement of indicator labeling reagent in the second area of high solute concentration allows for sustained release of indicator reagent, as sample fluid moves through this region, as the viscosity of the sample increases and the rehydration rate decreases. The sustained release of indicator reagent for the analyte facilitates low-end assay sensitivity by increasing both the time of incubation of the indicator labeling reagent with the analyte and the time of incubation of the bound indicator labeling reagent with the indicator capture reagent in the capture zone. This results in an increase in the amount of bound label to pass through the capture zone without increasing the maximum concentration of label to pass through the capture zone (and the number of false positive results) and without increasing the clearance time compared to an assay device in which the indicator reagent is placed only in a separate labeling reagent region.

Preferably where the first indicator labeling reagent and the second indicator labeling reagent are placed in separate porous regions of the device, the concentration of indicator labeling reagent in the separate labeling reagent region is lower than the concentration in the discrete zone of the analyte detection region. Preferably where the first indicator labeling reagent area and the second indicator labeling reagent area differ in solute concentration, the concentration of indicator labeling reagent which first comes into lateral flow contact with the sample will be lower than the concentration of indicator labeling reagent which subsequently comes into lateral flow contact with the sample.

Also, in this embodiment, preferably lateral flow contact of the sample with the first indicator labeling reagent in the separate labeling reagent region results in sustained release of the first indicator labeling reagent, while lateral flow contact of the sample with the second indicator labeling reagent in the labeling reagent zone of the analyte detection region results in quick release of the second indicator labeling reagent.

This device provides a simple, convenient assay method, with increased sensitivity and no increase in clearance time. This device is useful for detecting various analytes in a liquid sample.

Taking advantage of the test device of the present method, the device can be utilized with a method for detection of analytes directly from a biological sample, such as urine, blood, sputum, or material extracted from swabs or feces. In particular, the invention can be used to detect the presence or absence of human chorionic gonadotropin ("hCG") in urine. This detection is useful, in determining a positive or negative pregnancy in women. Alternatively, the invention can be used to detect the presence or absence of an antigen from streptococcus, for example, streptococcus pyogenes Group A, in material extracted from swabs of throat tissue.

In a first aspect of this invention, the separate sample receiving region is in contact with a separate labeling reagent region which is also made of a porous material which conducts liquid flow of the sample. The separate labeling reagent region is in contact with a separate analyte detection region. Lateral flow of the liquid sample will continue from the sample receiving region to the separate labeling reagent region to the analyte detection region. The analyte detection region contains a porous material which conducts lateral flow of the liquid sample. Preferably, the analyte detection region contains a discrete zone containing a second indicator labeling reagent which binds specifically to the analyte. The discrete zone and/or the separate labeling reagent region may also contain a mobile control labeling reagent.

The analyte detection zone also contains a capture zone. The capture zone is a discrete zone containing an immobile indicator capture reagent which can bind to the analyte or to the analyte-indicator labeling reagent complex. The capture zone may also contain a second capture reagent, i.e., a control capture reagent, which binds to the control labeling reagent.

Alternatively in a second aspect, the sample receiving region may be in direct contact with the analyte detection region which is in direct contact with a separate labeling reagent region (FIG. 2). In this configuration, the analyte detection region will be split into two portions. The first portion will contain the situs or zone for the indicator labeling reagent for the analyte, and the zone containing the control labeling reagent. The second portion of the analyte detection region will contain discrete zones containing the indicator capture reagent for the analyte and the control capture reagent.

In still another alternative embodiment, the sample receiving region may either contain a first indicator labeling reagent for the analyte (FIG. 3), or be positioned above the separate labeling reagent region containing a first indicator labeling reagent, in direct flow contact with the separate labeling reagent region. Alternatively, another separate porous region may be placed below the sample receiving region and above the separate labeling reagent region, to help direct flow of the sample to the separate labeling reagent region.

The analyte detection region is also in lateral flow contact with the end flow region. The end flow region contains a porous material which conducts lateral flow of the liquid sample. It is capable of absorbing excess liquid sample.

In the above aspect, the first indicator labeling reagent for the analyte (which is present in the separate labeling reagent region) and the second indicator labeling reagent (which is present in the discrete zone of the analyte detection region) are capable of forming a complex with the analyte. The analyte binding molecule can be the same or different in the first indicator labeling reagent and the second indicator labeling reagent.

The control labeling reagent is mobile but does not form a complex with either the analyte or the indicator capture reagent. The indicator capture reagent is capable of binding the analyte-indicator labeling reagent(s) complex, either by recognizing a binding site on the analyte or on the analyte-indicator reagent(s) complex. The control capture reagent is capable of binding the control labeling reagent.

In addition, preferably the porous materials in the above aspect are laminated with one continuous or separate semi-rigid material of at least 0.001 inches thick. The laminate covers the back only and provides adequate mechanical strength to the device, i.e., it provides support and strength characteristics to the porous material and overall device.

In a second aspect, the material used for the separate labeling reagent region enables the sustained release of the indicator labeling reagent, while the material used for the analyte detection region provides for quick release of the indicator labeling reagent.

Definitions

The term "analyte" as used herein refers to a compound or composition to be detected or measured in the test sample. The analyte will have at least one epitope that an antibody or an immunological reactive fragment thereof can recognize. Analyte can include any antigenic substances, haptens, antibodies and combinations thereof. The analyte of interest in an assay can be, for example, a protein, a peptide, an amino acid, a nucleic acid, a hormone, a steroid, a vitamin, a pathogenic microorganism for which polyclonal and/or monoclonal antibodies can be produced, a natural or synthetic chemical substance, a contaminant, a drug including those administered for therapeutic purposes as well as those administered for illicit purposes, and metabolites of or antibodies to any of the above substances. One preferred example of a hormone suitable for detection is human chorionic gonadotropin ("hCG"). Additional examples of preferred analytes are the pathogenic organisms streptococcus group A or B, or H. pylori. Other examples of preferred analytes are human antibodies against infectious agents such as HIV (used in diagnosis of AIDS), EBV (used in diagnosis of mononucleosis), or hepatitis virus, etc. Still other examples of preferred analytes are human proteins such as myoglobin, creatine kinase-MB, troponin-I, troponin-T or hemoglobin, etc.

The term "sample" as used herein refers to any biological sample that could contain an analyte for detection. Preferably the biological sample is in liquid form or can be changed into a liquid form. Preferably, the sample is a urine sample, or material extracted from a swab of throat tissue.

As used herein, the term "sample receiving region" means the portion of the assay device which is in direct contact with the liquid sample, i.e., it receives the sample to be tested for the analyte in question. The liquid sample can then migrate, through lateral flow, from the sample receiving region towards the end flow region. Preferably the sample receiving region is the edge of the assay device. The sample receiving region is in lateral flow contact with either the separate labeling reagent region or the analyte detection region.

This could either be an overlap or end-to-end connection. The sample receiving region may be impregnated with buffer to neutralize reagents in the sample during the lateral flow immunoassay.

The analyte in the sample must be capable of migrating, through lateral flow, with the liquid sample. The sample receiving region is made of porous material, preferably porous paper.

As used herein, the term "porous material" refers to any material capable of providing lateral flow. This would include material such as nitrocellulose, nitrocellulose blends with polyester or cellulose, untreated paper, porous paper, rayon, glass fiber, acrylonitrile copolymer or nylon. One skilled in the art will be aware of other porous materials that allow lateral flow. The term "lateral flow" refers to liquid flow in which all of the dissolved of dispersed components of the liquid are carried at substantially equal rates and with relatively unimpaired flow laterally through the material, as opposed to preferential retention of one or more components as would occur, e.g., in materials capable of adsorbing or imbibing one or more components.

The term "mobile" as referred to herein means diffusively or non-diffusively attached, or impregnated.

The reagents which are mobile are capable of dispersing with the liquid sample upon rehydration and carried by the liquid sample in the lateral flow. The term "immobile" as used herein refers to reagents which are attached to the support such that lateral flow of the liquid sample does not affect the placement of the immobile particle in the discrete region of the porous material. Such attachment can be through covalent, ionic or hydrophobic means. Those skilled in the art will be aware of means of attachment to immobilize various particles.

The term "labeling reagent" refers to a suitable reagent labeled with a chromogenic particulate such as colored latex, colloidal gold, selenium or the like. The term "labeling reagent" may refer either to an indicator labeling reagent or a control labeling reagent.

The term "indicator labeling reagent" refers to any particle, protein or molecule which recognizes or binds to the analyte in question, and which is conjugated or attached to a substance or particle capable of producing a signal that is detectable by visual or instrumental means. The attachment to the substance or particle capable of producing a signal may be chemical, covalent or noncovalent, ionic or non-ionic. Such labels producing a signal would include chromogens, catalysts, fluorescent compounds, colloidal metallic and nonmetallic particles, dye particles, enzymes or substrates, organic polymers, latex particles, liposomes with signal producing substances and the like. The particle or molecule recognizing the analyte can be either natural or non-natural, preferable monoclonal or polyclonal antibody.

Indicator labeling reagents may be, for example, a monoclonal or polyclonal antibody to the β-epitope of hCG, or a polyclonal or monoclonal antibody to the carbohydrate antigen of Streptococcus Group A. It is well known in the art that the carbohydrate antigen of Group A Streptococcus contains a repeated epitope. Thus, a sandwich complex can be formed even if the indicator capture reagent and the indicator labeling reagent each contain an antibody to the same epitope of Strep A.

The indicator labeling reagent may be bound to a label such as colored latex or gold sol particles. One of ordinary skill in the art will also appreciate that the label can be the same on the indicator labeling reagent and the control labeling reagent.

The mobile control labeling reagent is a particle or molecule which does not bind to the indicator capture reagent and is conjugated to a substance or particle capable of producing a signal. Preferably the control labeling reagent is BSA bound to a label such as colored latex or gold sol particles.

Alternatively, the control labeling reagent may be the same reagent as the indicator labeling reagent. In that embodiment, the "control capture reagent" is a reagent capable of binding the control labeling reagent but which does not bind to the analyte or the indicator labeling reagent-analyte complex. For instance, the control labeling reagent and indicator labeling reagent may be a rabbit anti-Strep A antibody linked to a label such as gold sol particles. In that embodiment, the capture reagent for the "control labeling reagent" also binds to the "indicator labeling reagent", but it does not bind the analyte. For instance, the control capture reagent for the positive control signal may be anti-rabbit γ-globulin antibody, while the indicator capture reagent of the analyte signal is an antibody to the Strep A antigen.

A "labeling particle" is a particle which contains a substance capable of producing a signal that is detectable by visual or instrumental means, e.g., a dye particle or latex particle containing a dye. Preferably the labeling particle is colored latex particles or gold sol.

The term "separate labeling reagent region" refers to a region which contains indicator labeling reagent. The separate labeling reagent region may also contain control labeling reagent. The separate labeling reagent region is preferably made of a mixture of cellulose and polyester, or other porous material.

The term "indicator capture reagent" as used herein refers to any particle or molecule which recognizes or binds the analyte in question. The indicator capture reagent is capable of forming a binding complex with the complex formed by the binding of the analyte to the indicator labeling reagent(s). The indicator capture reagent is immobilized to the porous material of the analyte detection region.

The capture reagent is immobile, i.e., is not affected by the lateral flow of the liquid sample due to the immobilization to the porous material. The particle of molecule of the indicator capture reagent can be natural, or non-natural, i.e., synthetic. Once the indicator capture reagent binds the analyte-indicator labeling reagent(s) complex it prevents the analyte-labeling reagent from continuing with the lateral flow of the liquid sample.

The term "control capture reagent" as used herein refers to any particle or molecule which is capable of binding the control labeling reagent which does not recognize or bind the analyte of question in the sample. For example, the control labeling reagent may be BSA conjugated to a label, such as colored latex, gold sol particles, or other labels known in the art.

The term "capture reagent" may refer to either the indicator capture reagent or the control capture reagent. The capture reagent may be applied to the porous material in any geometrical shape desired.

In one preferred embodiment, the control capture reagent would be a particle or molecule which recognizes or binds the BSA conjugated to the labeling particle. Preferably, the control capture reagent would be a monoclonal or polyclonal antibody which recognizes BSA. Just as the indicator capture reagent is immobilized in a discrete situs on the porous material of the analyte detection region, the control capture reagent is also immobilized in a discrete situs on the porous material of the analyte detection region. Once it binds the control labeling reagent it immobilizes the control labeling reagent and prevents it from continuing lateral flow with the liquid sample. Binding of the immobilized capture control reagent to the control labeling reagent results in the formation of a positive control signal, which serves as an internal control that the assay was performed properly.

The term "clearance time" refers to the time that it takes for a sufficient amount of unbound indicator labeling reagent to flow through the capture zone so that the background is sufficiently reduced compared to the capture zone band intensities to permit an accurate reading of the positive and negative results. Unbound indicator labeling reagent in the capture zone may lead to higher background and false positives. The clearance time reflects the time that it will take for the assay to be completed.

The term "analyte detection region" as used herein refers to the portion of the assay device which is in lateral flow contact with the end flow region, and either the porous material of the sample receiving region or the porous material of the separate labeling reagent region. The contact can be an overlap or end-to-end connection. The analyte in the sample must be capable of migrating through lateral flow with the liquid sample. The analyte detection region is made of a porous material just as the sample receiving region is. Preferably, the analyte detection region is made of nitrocellulose. The sample receiving region, the separate labeling reagent region, the analyte detection region and the end flow region can be made of different material. The analyte detection region can contain the mobile labeling reagents, the immobile indicator capture reagent and the immobile control capture reagent. In other embodiments, the analyte detection region contains only the immobilized control capture reagent and the indicator capture reagent.

The term "discrete zone", "discrete capture situs" or "discrete control situs" as used herein refers to a defined area in which either the labeling reagents, the indicator capture reagent or the control capture reagent are impregnated (for the indicator labeling reagents and control labeling reagents) or immobilized (for the control capture or indicator capture reagents) to the porous material. The discrete capture situs of the control capture reagent or the indicator capture reagent for the analyte provide a discrete visible signal in a desired geometric shape from which to view the results of the test. For example, if the one labeling reagent is analyte bound to anti-analyte conjugated to Blue latex label, then a discrete blue signal will appear at the discrete capture situs if the indicator capture reagent binds and immobilizes the analyte-labeling reagent complex. If the control labeling reagent is BSA conjugated to a label such as colored latex or gold sol, then a discrete signal will form at the discrete control situs if the control capture reagent has immobilized the BSA-control labeling reagent.

The term "end flow region" as used herein refers to the portion of the assay device which is in lateral flow contact with the analyte detection region. The liquid sample migrates to the end flow region. It is capable of absorbing excess liquid sample. The contact with the analyte detection region can be either by overlap or end-to-end connection. This region is made of porous material, usually porous paper.

The term "top" refers to the upper surfaces of the regions of the device, e.g., the top surface of the test strip.

The term "semi-rigid" as used herein refers to the material used to support the porous material of the device. This can be one continuous piece of laminate or separate pieces. The laminate is preferably a vinyl plastic but one skilled in the art will recognize that numerous materials can be used to provide the semi-rigid support, which is preferably at least 0.001 inches thick. This includes polyester, polycarbonate, methyl methacrylate polymer, polystyrene, polyethylene, polypropylene, and waxed cardboard. The semi-rigid material must at least be of 0.001 inches thick in order to produce the desired adequate mechanical strength or support for the device to function effectively.

The term "adequate mechanical strength" as used herein refers to a desired support to the assay device so as to function properly. The adequate mechanical strength is the support achieved for the entire assembled assay device so as to function properly in the collection and analysis of the analyte in the liquid sample. The total thickness of all of the layers of the immunoassay device is preferably at least 0.003 inches thick. The total thickness of the immunoassay device consists of the thickness of the backing, the membrane elements, label pads (if desired), and the cover. This minimum total thickness is required in order to produce the desired adequate mechanical strength or support for the device to function effectively.

The laminate covers the back only and provides adequate mechanical strength to the device, i.e., it provides support and strength characteristics of the porous material and overall device such that lateral flow of liquid through the device will not be interrupted, for instance by the collapse or disintegration of the device upon wetting. Additional support for the device during the immunoassay may be provided by the walls of a test tube against which the device may rest during the lateral flow.

The term "plastic material," or "plastic cover," or "cover" as used herein refers to any plastic material which can cover the porous material of the device. Preferably, this is mylar, however, those skilled in the art will know of various materials that can be used for such purposes. The cover can be one continuous plastic or separate pieces as shown in the figures. It must allow the discrete control and discrete capture situses to be viewed. Thus, if the cover is clear then the result can be viewed through the clear cover. If the cover is not clear, then a window, gap or hole must be used so the results can be viewed. In addition, the cover must leave a portion of the sample receiving region exposed so the sample can be applied to the receiving region.

Alternatively, the backing and plastic cover can be a molded plastic housing.

Other features and advantages of the invention will be apparent from the following detailed description of the presently preferred embodiments of the invention in conjunction with the accompanying drawings and from the claims.

DESCRIPTION OF THE DRAWINGS

FIG. 16(a) shows a positive result. A test signal line is formed by binding of the indicator capture reagent to the indicator labeling reagent-strep A complex. A positive control line is formed by binding of the control capture reagent to the control labeling reagent.

FIG. 16(b) shows a negative result. Only a positive control line is formed by binding of the control capture reagent to the control labeling reagent.

FIG. 16(c) shows an invalid result. If no positive control line has appeared or the background is too high and it is not possible to see the positive control signal, the result is invalid.

The drawings are not necessarily to scale, and certain features of the invention may be exaggerated in scale and shown in schematic form in the interest of clarity and conciseness.

DETAILED DESCRIPTION OF THE INVENTION

The following are examples of the immunochromatograhic assay device of the present invention. These examples are offered by way of illustration and are not intended to limit the invention in any manner.

Figure 1:
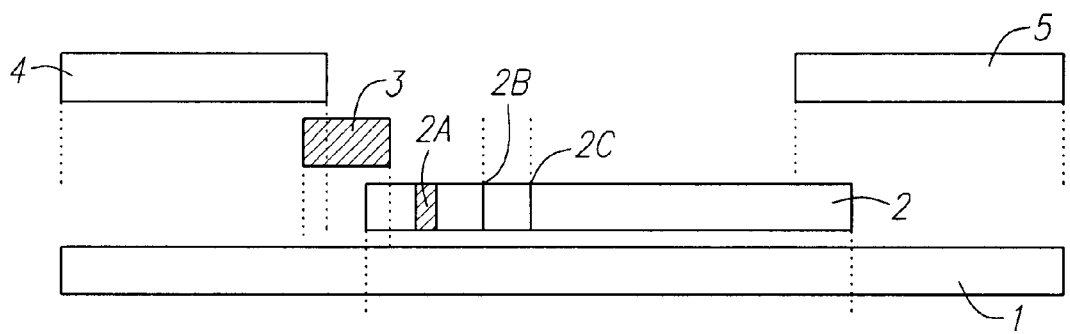
FIG. 1 illustrates an expanded perspective view of the immunochromatographic elements assembled into a test device according to the present invention.

FIG. 1 depicts an exemplary embodiment of the invention. A series of porous material pieces (2), (3), (4), and (5) are laminated to an elongated strip of a semi-rigid material (1), such as vinyl and the like.

The separate sample receiving region (4) is a porous material, preferably paper or a mixture of cellulose and polyester. In the preferred embodiment shown in FIG. 1, the separate sample receiving region is in direct liquid flow contact with the separate labeling reagent region (3). This contact may be lateral flow contact, as shown in FIG. 1. Alternatively, this contact may be perpendicular flow contact, with the separate sample receiving region placed on top of the separate labeling reagent region (not shown). The separate labeling reagent region is in direct lateral flow contact with the analyte detection region (2). The analyte detection region contains a discrete zone containing the mobile labeling reagent (2a). This labeling reagent is the same reagent found in the separate labeling reagent region (3), which is capable of binding to the analyte.

Figure 9:
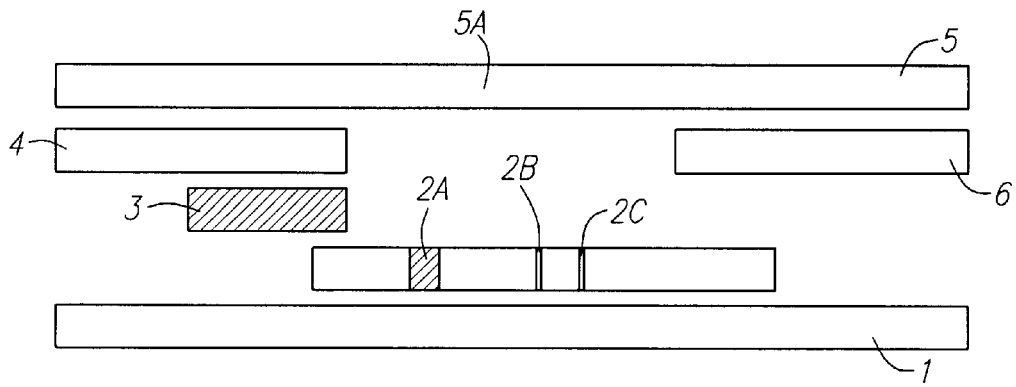
FIG. 9 illustrates an expanded perspective view of the immunochromatographic elements assembled into a test device according to a preferred embodiment of the present invention.
Figure 10:
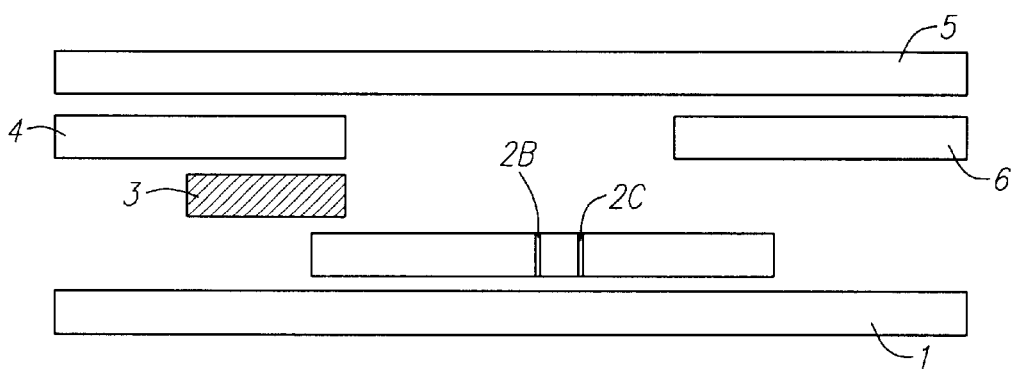
FIG. 10 illustrates an expanded perspective view of the immunochromatographic elements assembled into a test device according to an alternative preferred embodiment of the present invention.
Figure 11:
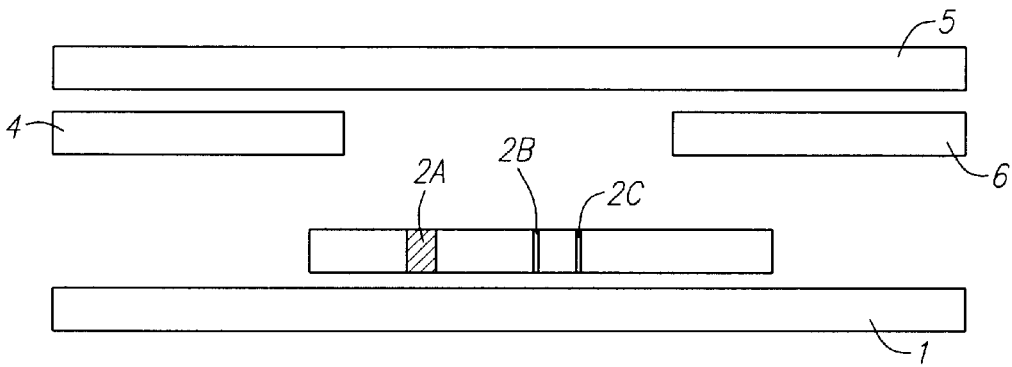
FIG. 11 illustrates an expanded perspective view of the immunochromatographic elements assembled into a test device according to another alternative preferred embodiment of the present invention.
Figure 12:
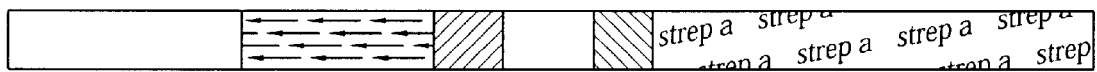
FIG. 12 illustrates an upper view of the test device constructed according to the present invention having upper covering printed with product information.
Figure 13:
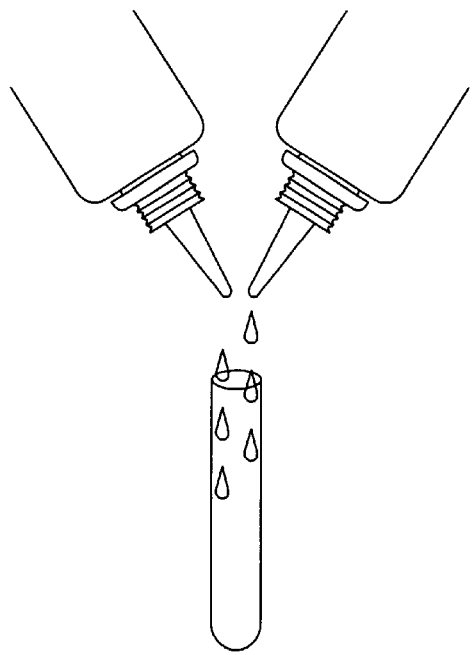
FIG. 13 illustrates the mixing of reagents in a test tube.
Figure 14:
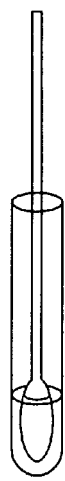
FIG. 14 illustrates placement of a throat swab into the test tube containing the reagents.
Figure 15:
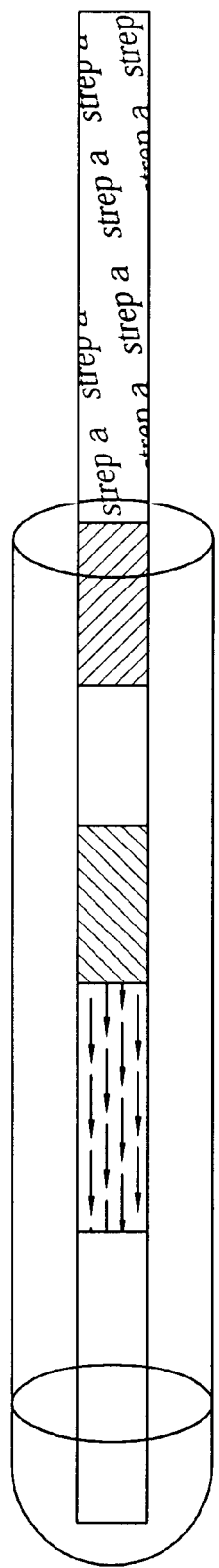
FIG. 15 illustrates the placement of the device into the test tube containing the solubilized sample.
Figure 16A:
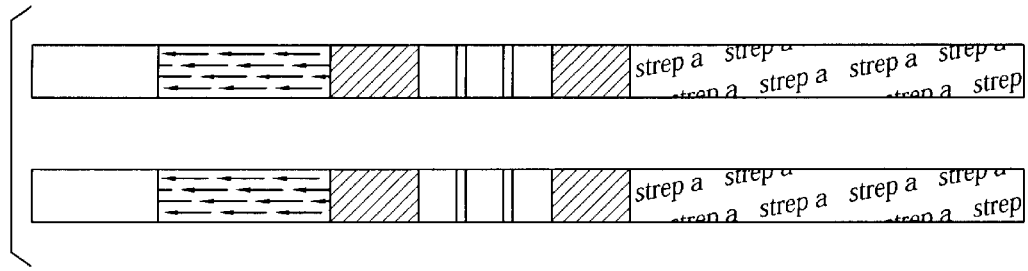
FIGS. 16(a)–(c) illustrate the interpretation of results.
Figure 16B:
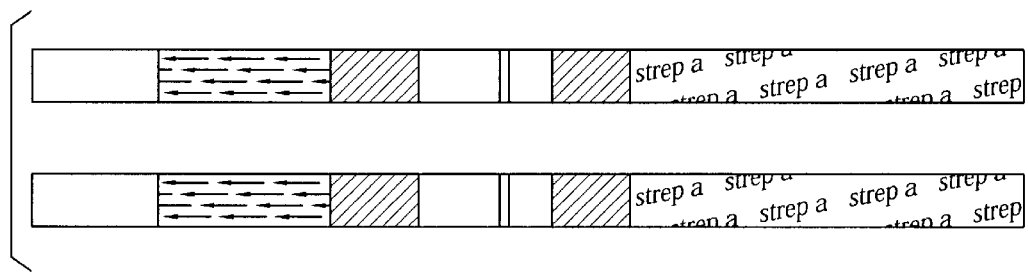
Figure 16C:
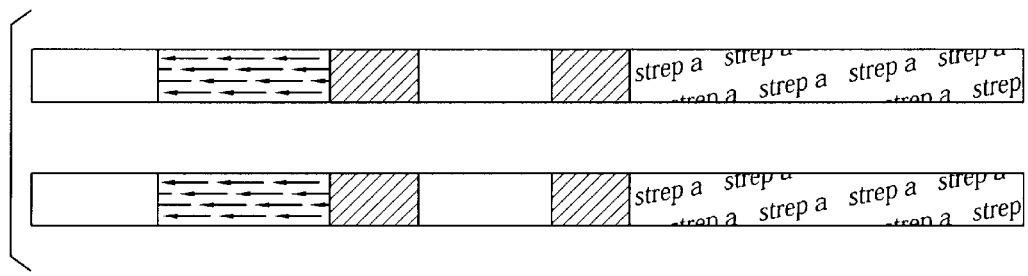

In the embodiment shown in FIG. 9, the separate labeling reagent region is in direct lateral flow contact with the analyte detection region (2).

In this embodiment, the analyte detection region (2) of the immunochromatographic assay device contains two mobile labeling reagent in a discrete situs (2a), an immobile indicator capture reagent in a discrete situs (2b) and an immobile control capture reagent at a discrete situs (2c). The mobile labeling reagent consists of a first mobile labeling reagent which can bind the analyte to be detected, i.e., an indicator labeling reagent. Preferably the indicator labeling reagent is a monoclonal or polyclonal antibody that specifically binds the analyte to be detected. Attached to the antibody, either covalently or noncovalently, is a substance or particle capable of producing a signal detected visually. Such particles used as labeling particles can be colloidal gold, dye sols, colored latex and the like. Preferably, the label is colored latex (blue) or gold sol. One skilled in the art will recognize suitable labeling particles. The second mobile labeling reagent is a particle or molecule which does not recognize the analyte and is conjugated to a substance or particle capable of producing a signal, i.e., control labeling reagent. Preferably, the control labeling reagent is BSA conjugated to colored latex (Red) or gold sol.

The mobile indicator labeling reagent in the analyte detection region may be the same indicator labeling reagent found in the separate labeling reagent region (3), which is capable of binding to the analyte. A strip of plastic material (5), preferably clear mylar, is covered on top of the device. Portion (5a) can be a window or clear so as to permit viewing of the capture and control discrete situses, i.e., to permit viewing of the results. An end flow region (6) is in lateral flow contact with the analyte detection region.

Figure 2:
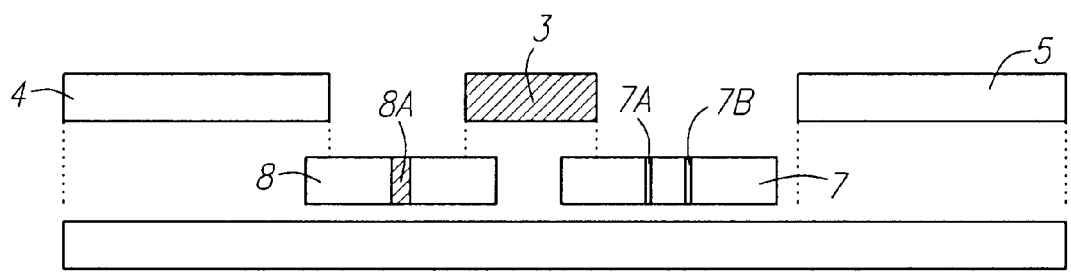
FIG. 2 illustrates an expanded perspective view of the immunochromatographic elements of the present invention with an alternative placement of the separate labeling reagent region and labeling reagent present in the discrete zone of the lateral flow porous material.

In the preferred embodiment shown in FIG. 2, the separate sample receiving region (4) is in direct lateral flow contact with the portion of the analyte detection region (8) which contains the discrete zone or zones containing the indicator labeling reagent and control labeling reagent (8a). This portion of the analyte detection region is in direct lateral flow contact with the separate labeling reagent region (3). The separate labeling reagent region is in direct lateral flow contact with the portion of the analyte detection region (7) containing the capture zones (7a and 7b).

The second portion of the analyte detection region (7) is in direct lateral flow contact with the separate end flow region (5). The assembly is such that there is end-to-end contact of each region or overlaps sufficiently to provide continuous wicking action (i.e., continuous lateral flow). A strip of plastic material, preferably clear mylar, may be covered on top of the device leaving a portion of the front pad exposed for sample application (not shown).

In an assay using the device shown in FIG. 9, the sample receiving region (4) of the assay device is directly placed into a sample containing extracted analytes, for example, a processed throat swab sample which may contain extracted Streptococcus Group A carbohydrate antigen, or a urine stream which may contain hCG. The sample flows laterally along the porous material region by capillary action and migrates past the separate labeling reagent region (3), and then past the labeling reagents in the analyte detection region (2a). The presence and/or the amount of analyte in the sample may then be determined by the visibility of a signal line (2b) formed by the specific binding of the immobilized indicator capture reagent to the analyte-indicator labeling reagent conjugate complex.

The appearance of a second signal (2c) may be utilized as a built-in positive control signal. This positive control signal results from binding of the immobilized control capture reagent to the control labeling reagent, e.g., BSA-Red latex. If the reagents and assay are working properly, then a red signal line will appear at (2c) the discrete control situs. The red control line is an internal control. The test stick must absorb the proper amount of the sample and the test stick must be working properly for the red control line to appear. For the test stick to be working properly, the capillary flow must occur. Thus, the control line serves as an indication that the proper amount of reagents have been added to the assay chamber, and that sufficient lateral flow has occurred for the control labeling reagent to reach the control capture reagent zone.

The results of an assay can then be observed through a viewing window (5a) covered by clear mylar.

Figure 3:
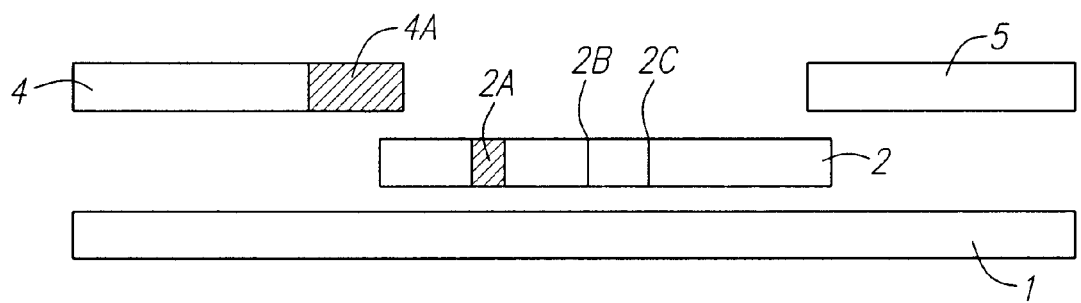
FIG. 3 shows another embodiment of the present invention where the discrete zone containing labeling reagent is located on the separate porous piece containing the sample receiving region.

In the embodiment shown in FIG. 3, there is no separate labeling reagent region. Mobile indicator labeling reagent and control labeling reagent are placed in the analyte detection region (2a). In addition, labeled reagent (4a) can be impregnated near one end of the sample receiving region (4).

In embodiments where the sample receiving region is in direct contact with the analyte detection region, illustrated in FIG. 2, the analyte detection region may be split into two portions (7) & (8). In this embodiment, the first portion of the analyte detection region (8) is in direct contact with the sample receiving region (4). The first portion of the analyte detection region contains a discrete zone containing the mobile indicator labeling reagent and control labeling reagent (8a), and is also in lateral flow contact with the separate labeling reagent region (3). The separate labeling reagent region (3) is in contact with the second portion of the analyte detection region (7), which contains the immobilized indicator capture reagent and control capture reagent (7a) & (7b). The second portion of the analyte detection region is in direct flow contact with the end flow region (5).

Other layouts, for instance, of the upper covers or the labeled particles are possible, as long as lateral flow of the porous membranes is permitted. Overlap or end-to-end connection can be used as long as lateral flow occurs. Alternatively, the various regions of the test strip may also be placed on a single porous member.

For example, the control labeling reagent and indicator labeling reagent may be placed only in a region of the analyte detection region, and the separate labeling reagent region may be omitted. Alternatively, the control labeling reagent and the indicator labeling reagent may be placed only in a separate labeling reagent region, and additional indicator labeling reagent or control labeling reagent may be omitted from the analyte detection zone.

Thus, the present invention comprising an immunochromatographic assay device increases the range of sensitivity without increasing the clearance time or increasing the incidence of false positives. Thus the devices of this invention can be used to perform quick, highly sensitive assays. In addition, the advantage of using a same basic design with universal applicability for different analytes also promotes the objective of inventory reduction.

One Exemplary Assay Device

Dimensions and construction of an immunoassay device have been previously described in U.S. application Ser. No. 08/444,238 invented by Ching Huang and Eugene Fan, entitled One Step Immunochromatographic Device and Method of Use. These procedures can be adapted in assembling the devices of this invention using the following dimensions. For instance, the sample aapplication region can be shortened to accommodate the length of a separate indicator reagent region.

Dimensions of the Exemplary Assay Device

| | |
|---|---|
| Upper Covering: | 4 mm × 98 mm |
| Lower Backing: | 4 mm × 98 mm |
| Separate Labeling Reagent Region: | 4 mm × 5 mm |
| Sample Receiving Region: | 4 mm × 20 mm |
| End Flow Region: | 4 mm × 56 mm |
| Analyte Detection Region: | 4 mm × 25 mm |
| Viewing Window: | 4 mm × 9 mm |

Figure 4:
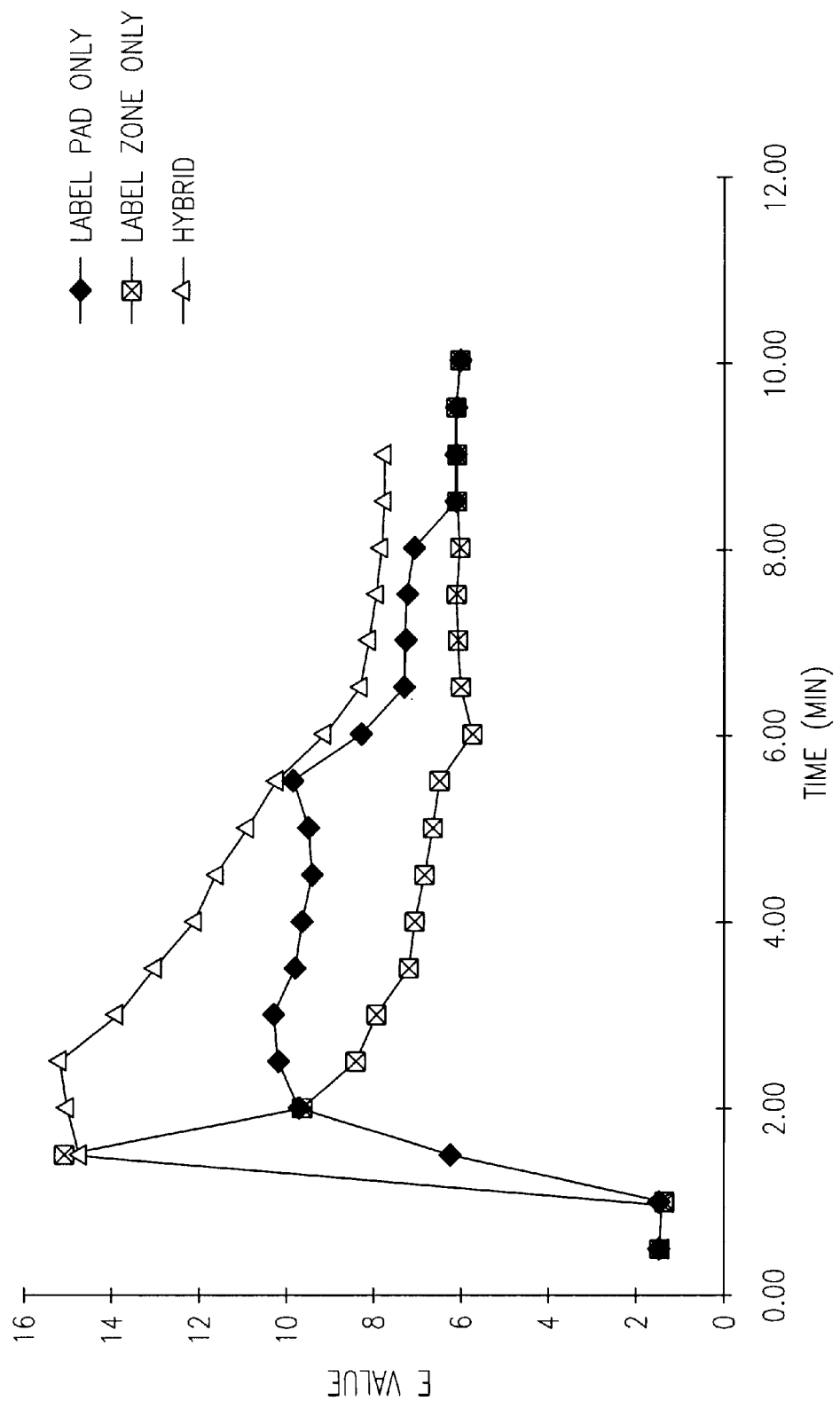
FIG. 4 is an intensity curve graph showing the intensity of the dye used as a labeling reagent passing through the capture zone at various time points for three devices containing different arrangements of the labeling reagent.

(Note: Product information may be printed on the upper covering as shown in FIG. 4.)

The device is required to have an adequate total mechanical strength (as defined above and discussed below) in order for the device to function without disruption of lateral flow.

Selection of Materials for the Exemplary Device

1. Analyte Detection Region: Important features of the material are its ability to wick fluids and to bind proteins. Exemplary materials include nitrocellulose, nylon or the like. In a preferred embodiment of this invention, the material is nitrocellulose with or without laminated solid support such as polyester. Nitrocellulose is readily available from numerous suppliers.

2. Sample Receiving Region: Suitable materials include cotton, cellulose, mixed fibers, glass fiber and the like. For example, paper such as 470 and 740-E from Schleicher and Schuell, Keen, N.H., or D28 from Whatman, Fairfield, N.J., can be selected for its high fluid absorption and wicking speed. A more porous material such as glass fiber #66078 from Gelman Sciences, Ann Arbor, Mich., or "POREX" from Porex Technologies, Fairburn, Ga., is suitable for impregnating labeled particles.

3. Separate Labeling Reagent Region: A good candidate would be a porous material which allows the ease of releasing the impregnated labeling reagents from the region. Such materials include glass fiber from Gelman Sciences, Ann Arbor, Mich., or Accuwik from Pall BioSupport, Port Washington, N.Y.

4. Backing Supports: For the present invention, the preferred materials are clear mylar with thickness about 0.001 inches to 0.010 inches for the upper covering and white vinyl with thickness about 0.001 inches to 0.030 inches for the lower backing. Both the mylar and the vinyl sheets have adhesive on one side so as to attach the porous material. Materials such as mylar, polyester, and vinyl with adhesive are readily available.

5. Labeling Reagents: A chromogenic particulate such as colored latex, colloidal gold, selenium or the like is labeled with a suitable reagent specific for the targeted analyte. For the present invention, the preferred chromogenic particulate is colored latex or gold sol. More preferably, blue or red colored latex or gold sol is used. Latex and gold sol are commercially available from a number of sources.

6. End Flow Region: Suitable materials include cotton, cellulose, mixed fibers, glass fiber and other like materials with high fluid absorption capacity. For example, paper such as 470 and 740-E from Schleicher and Schuell, Keen, N.H., or D28 from Whatman, Fairfield, N.J., can be selected for its high fluid absorption and wicking speed.

7. Antibodies:

A. Strep A antibody: New Zealand white rabbits were injected with partially purified Group A Streptococcus antigen. The rabbits which produced a high titer of antibody were identified by an enzyme immunoassay method. The sera from these rabbits were pooled and purified through Strep A antigen affinity column.

B. Anti-BSA Antibody: Affinity purified sheep anti-BSA antibody was obtained from Bethyl Lab, Montgomery Tex.

C. Monoclonal anti-β-hCG antibody: The monoclonal anti-β-hCG antibody can be obtained from Medix Biotech (San Carlos, Calif.), Medix Biochemica (Kauniainen, Finland), or other commercial sources. The affinity purified polyclonal anti-α-hCG antibody (rabbit) can be purchased from Bioreclamation (East Meadow, N.Y.), H.T.I. Bio-Products, Inc. (Ramona, Calif.) and other sources. As is discussed below, the capture reagent recognizes the β-epitope of hCG while the control agent recognizes the α-epitope of hCG, or vice versa.

8. Preparation of Latex Conjugates

The basic protocol for conjugation of protein to latex, by simple adsorption or by covalent binding, is well known in the art and is hereby incorporated by reference.

For example, the indicator labeling reagent may be an anti-Group A streptococcus antibody conjugated with blue latex, while the indicator capture reagent may be an anti-Group A streptococcus capture antibody.

Blue carboxylated latex particles (0.2 to 0.5 microns) were activated with 0.2% EDAC in the presence of 0.1% sulfo-NHS in 20 mM MES buffer, pH 5.5, for 30 minutes at room temperature. The excess amount of reagents were removed by washing in an Amicon Concentrator. The activated latex particles were resuspended in 2 mM MES buffer, pH 6.5 to a concentration of 0.5%, and a ratio of 0.05 mg Strep A antibody were added to 1 mg of latex. The mixture was incubated at room temperature for 2 hours. After incubation, the conjugated latex was washed again to remove free antibody. The antibody-latex conjugate was then sonicated, filtered, and resuspended in buffer containing 50 mM Tris, pH 8.5; 20% sucrose; 2.0% casein, and 0.1% sodium azide.

The conjugation of BSA to red carboxylated latex (size of 0.2 to 0.5 microns) was essentially the same as described above except replaced the blue latex with red latex and Strep A antibody with BSA.

9. Preparation of Latex Coating Solution

The blue latex solution and the red latex solution were mixed at a ratio from 5:1 to 1:1 depends upon the sensitivity of the conjugate and intensity of red control line desired. The preferable ratio is approximate 1:1. These solutions are then impregnated into the porous material using methods well known in the art, all of which are hereby incorporated by reference.

10. Coating of Capture Reagents on the Discrete Situses of the Analyte Detection Region Thin lines of the indicator capture reagent or control capture reagent were applied on the material using airbrush techniques (Iwata, model HP-BC2). The width of the lines can be 0.2 mm to 2 mm, a width of 1 mm is preferred. Such material is immobilized by techniques well known in the art, hereby incorporated by reference.

11. Coating of Latex Conjugate (Labeling Reagents) on the Analyte Detection Region Immediately after the capture reagents were applied on the material. The latex solution can be applied on the material by using airjet techniques such as BioDot Biodoser machine from Bio-Dot, Inc., Irvine, Calif. The membrane strip is then dried in a force air oven at 70° C. for 45 minutes. Such application allows the labeling reagents to be mobile.

12. Preparation of Separate Labeling Reagent Region

The separate labeling reagents region is prepared by saturating a piece of porous material such as Accuwik with the prepared latex coating solution. The latex solution containing the indicator labeling reagent for the analyte was applied to ACCUWIK™ AW14-20S4 (Pall BioSupport, Part Washington, N.Y.) at saturation volume and then dried in a forced air oven at 70° C. for 30 minutes. Labeling reagent applied by this method will remain mobile.

13. Preparation of Sample Receiving Region

In this invention, the sample receiving region may not only absorb and transport liquid sample, it may also functions as a specimen collection apparatus and as a buffering agent or a neutralizing agent for an acidic extraction solution. The sample receiving region may comprise a paper treated with buffer, detergents, blocking proteins and the like to facilitate movement of dried latex particles or to reduce nonspecific binding of the assay. In the case of the Strep A assay, 740E paper was soaked in a buffer solution, dried, and then assembled into the assay device. Specifically, buffer solution containing 1.5% zwittergent 3–12, 0.1% sodium azide, 0.1% rabbit gamma globulin, 0.1 M NaCl and 0.2 M Tris, pH 9.0 was used.

In the case of the hCG assay, an appropriate amount of buffer solution was dispensed to the separate labeling reagent region (labeling pad), dried, and then assembled into the assay device. Specifically, 0.4 mL of buffer solution containing 4% zwittergent 3–12, 1% rabbit gamma globulin, 1% casein and 200 mM Tris, pH 8.5 were applied on 254 mm long strip of front pad at it's edge. The sample receiving region is then dried in a forced air oven at 70° C. for 15 minutes.

14. Assembly of the Assay Device

A sheet of white vinyl (98 mm×254 mm) is placed on a flat surface. The cover paper on the white vinyl sheet is removed to expose the adhesive. A strip of the analyte detection region (925 mm×254 mm) containing latex and antibody lines is attached to the white vinyl sheet. A strip of the sample receiving region (20 mm×254 mm) is attached to the left edge of the white vinyl sheet. A separate labeling reagent region (5 mm×254 mm) is layered between the sample receiving region and the white vinyl sheet. The internal ends of the separate labeling reagent region and the sample receiving region are lying flush, and overlapping the analyte detection region by 1.5 mm. The end flow region (56 mm×254 mm) is attached to the right edge of the white vinyl sheet while overlapping about 1.5 mm on top of the analyte detection region. The cover paper from the clear mylar sheet is removed (98 mm×254 mm) to expose the adhesive. Centering the window region of the clear mylar sheet over the capture reagent lines in the analyte detection region, the clear mylar sheet is attached with the adhesive side down on top of the end flow region, analyte detection region and sample receiving region. The whole sheet is pressed with a roller to ensure the lamination is secure. The laminated sheet is then cut to 4 mm wide sticks.

In yet another aspect, the present invention comprising an immunochromatographic assay device without molded plastic casings greatly reduces the cost for manufacturing. In addition, the advantage of using a same basic design with universal applicability for different analytes also promotes the objective of inventory reduction.

EXAMPLE 1

One-Step Immunoassay for Strep A Which Does Not Require Sample Manipulation

Most preferably the one-step assay device will contain an OSOM™ Strep A Test . The OSOM™ Strep A Test detects either viable or nonviable Group A Streptococcus organisms directly from a throat swab, providing results within 5 minutes.

Specimens may be collected with a sterile swab from the tonsils and/or the back of the throat, taking care to avoid the teeth, gums, tongue or cheek surfaces. Sterile swabs may be used to collect the specimens. Preferably sterile rayon or dacron swab are used to collect specimens. Alternately, swabs with transport tubes containing liquid media can also be used. Preferably the liquid media used in transport tubes will be Modified Stuart's Transport Media ("CULTURETTE" available from Becton Dickinson).

The OSOM™ Strep A Test can be used for the qualitative detection of Group A Streptococcal antigen from throat swabs or confirmation of presumptive Group A Streptococcal colonies recovered from culture.

The assays as described provide a method for antigen extraction from the sample and introduction of the device into the sample containing extracted analytes without the need for specimen manipulation following the extraction. This provides an advantage of a more rapid and convenient test procedure to the user.

Test Procedure for running the OSOM StreD A Test:

Just before testing, 3 drops Reagent 1 (2M sodium nitrite) (pink) and 3 drops Reagent 2 (0.3 M acetic acid) were added to the Test Tube (the solution should turn light yellow). The swab (PurFybr Inc., Munster, IN) was immediately inserted into the tube. Vigorously mixing of the solution by rotating the swab forcefully against the side of the Tube at least ten times. (Best results were obtained when the specimen was vigorously extracted in the solution.) The samples were left standing for one minute. As much liquid as possible was expressed from the swab by pressing the swab firmly against the side of the Tube. The swab was discarded. An OSOM™ Strep A Test Stick was then placed into the extracted sample. The results were read at 5 minutes.

Comparison of the Sensitivity of Results of the OSOM™ Assay for Streptococcus Group A and Other One-Step Assays Procedure:

Strep A cells were picked up from a pure culture plate and suspended in saline solution. Subsequent serial dilutions were made with saline to yield different concentrations of cell suspension. The cell concentration was determined by the optical density method. $OD_{650}$ of 1 is equivalent to approximately $2\times10^9$ cells/mL in suspension. 25 µL of the suspension was pipetted onto the tip of each of the swabs supplied by the manufacturers. Tests were performed within 5 minutes after the swabs were spiked with cell suspension. Tests were performed by following procedure described in each prospective manufacturer's directional insert.

Results:

| Cell Qty/Swab | $4 \times 10^7$ | $4 \times 10^6$ | $8 \times 10^5$ | $4 \times 10^5$ |
|---|---|---|---|---|
| Wyntek OSOM ™ | Positive | Positive | Weak Positive | Weak Positive |
| Quidel | Positive | Positive | Weak Positive | Negative |
| Binax | Positive | Positive | Negative | Negative |

These results indicate Wyntek OSOM™ Strep A Test can detect Group A Streptococcus cells when present at a concentration as low as $4\times10^5$ cells per swab, while Quidel's and Binax's tests can only detect Strep A cells when present at a concentration of $8\times10^5$ cells per swab or $4\times10^6$ cells per swab, respectively.

Performance of OSOM™ Strep A Test in Clinical Trials

In a multi-center evaluation, a total of 639 throat swabs were collected from patients presenting with pharyngitis. Each swab was inoculated to a sheep blood agar plate, then tested by the OSOM Strep A Test. Plates were incubated for 18–24 hours at 350–37° C. at 5–10% $CO_2$ with a Bacitracin disk. Presumptive GAS colonies were confirmed with commercially available Strep A testing kits.

Of the 639 total specimens, 464 were found to be negative by culture and 454 were also negative by the OSOM Strep A Test, for a specificity of 97.8%. Of the 175 specimens found to be positive by culture, 168 were also positive by the OSOM Strep A Test, for a sensitivity of 96.0%. The 95% confidence intervals were calculated to be 96.6–99.0% for specificity and 94.4–97.6% for sensitivity. Overall agreement between culture and the OSOM Strep A Test was 97.3% (622/639). The results are summarized below:

| Culture Classification | OSOM/Culture | % Correct |
| --- | --- | --- |
| Negative (Specificity) | 454/464 | 97.8% |
| 1+ (≦10 colonies) | 3/6 | 50.0% |
| 2+ (11–50 colonies) | 9/13 | 69.2% |
| 3+ (>50 colonies) | 44/44 | 100% |
| 4+ (predominant growth) | 112/112 | 100% |
| Total Positive (Sensitivity) | 168/175 | 96.0% |
| Total (Overall Agreement) | 622/639 | 97.3% |

In addition, the OSOM Strep A Test was used to confirm the identification of Group A Streptococcus on blood agar plates. As a culture confirmation test, the OSOM Strep A Test was 100% sensitive (62/62) and 100% specific (39/39).

The following organisms tested at levels of approximately $1 \times 10^8$ organisms/test were all found to be negative when tested with the OSOM Strep A Test:

Streptococcus Group B
Streptococcus Group C
Streptococcus Group F
streptococcus Group G
*Streptococcus pneumoniae*
*Streptococcus sanguis*
*Streptococcus mutans*    *Enterococcus faecalis*
*Staphylococcus aureus*
*Staphylococcus epidermidis*
*Corynebacterium diptheria*
*Serratia marcescens*
*Candida albicans*
*Klebsiella pneumoniae*    *Pseudomonas aeruginosa*
*Bordetella pertussis*
*Neisseria meningitides*
*Neisseria gonorrhoeae*
*Neisseria sicca*
*Neisseria subfiava*
*Branhamella catarrhalis*
*Hemophilus influenza*

EXAMPLE 2

Procedure for Testing the Presence or Absence of Human Chorionic Gonadotropin (hCG) in Liquid Samples Samples containing hCG were applied to the sample receiving region of the assay device. The device is then placed on a paper towel. Within one minute, the test result, if positive for hCG, will appear as one blue line together with one red line. If only a red line appears then the results are negative. The red latex is used as a control to ensure the assay reagents are working and that lateral flow is occurring. Determination of Clearance Times and Relative Sensitivities Three types of devices were assembled: (1) devices with labeling reagent (referred to in this example as a label) placed only in a separate labeling reagent region (referred to in this example as a label pad); (2) devices with label reagent placed only in a discrete labeling zone of the analyte detection region (referred to in these examples as the label zone); and (3) a hybrid device with labeling reagent placed in both the label zone and the label pad (referred to in these examples as "the hybrid"). The triplicate strips were run by application of a negative control sample solution to the sample pad. The color development at the capture zone was measured with the CR-241 at 30 second intervals for approximately 10 minutes.

At various time points, the reflectiveness (E values) intensity at the capture zone was recorded using a Minolta Chroma Meter CR-241.

Table 1 shows the intensities (E) at the capture zone at various time points for the three types of devices. The hybrid device contains the same amount of dye in the label pad as the device containing dye only in the label pad; the hybrid device also contains the same amount of dye in the label zone as the device containing dye only in the label zone.

TABLE 1

| | E Values | | |
| --- | --- | --- | --- |
| Time (min) | Label Pad Only | Label Zone Only | Hybrid |
| 0.50 | 1.64 | 1.55 | 1.56 |
| 1.00 | 1.63 | 1.49 | 1.48 |
| 1.50 | 6.36 | 15.01 | 14.75 |
| 2.00 | 9.75 | 9.65 | 15.02 |
| 2.50 | 10.2 | 8.45 | 15.19 |
| 3.00 | 10.3 | 7.97 | 13.88 |
| 3.50 | 9.82 | 7.25 | 12.97 |
| 4.00 | 9.66 | 7.09 | 12.1 |
| 4.50 | 9.42 | 6.87 | 11.58 |
| 5.00 | 9.49 | 6.67 | 10.91 |
| 5.50 | 9.81 | 6.48 | 10.12 |
| 6.00 | 8.27 | 5.72 | 9.16 |
| 6.50 | 7.31 | 5.98 | 8.7 |
| 7.00 | 7.26 | 6.02 | 8.33 |
| 7.50 | 7.2 | 6.06 | 8.14 |
| 8.00 | 7.05 | 6 | 7.95 |
| 8.50 | 6.1 | 6.02 | 7.84 |
| 9.00 | 6.1 | 6.02 | 7.75 |
| 9.50 | | 6.06 | 7.74 |
| 10.00 | | 5.96 | 7.73 |
| 10.50 | | | 7.74 |
| 11.00 | | | |
| 11.50 | | | |
| 12.00 | | | |

When the sample is applied, lateral flow mobilizes the labeling reagent. As the reagent begins to pass the capture zone, the measured intensity increases. As some 30 of the labeling reagent is mobilized, the amount of labeling reagent remaining in the separate labeling reagent region and/or in the discrete zone begins to decrease. Gradually the amount of labeling reagent passing the capture zone begins to decrease until it falls sufficiently to permit accurate reading of the positive and negative results. The clearance time is an important factor in determining the time necessary to complete the assay.

Figure 5:
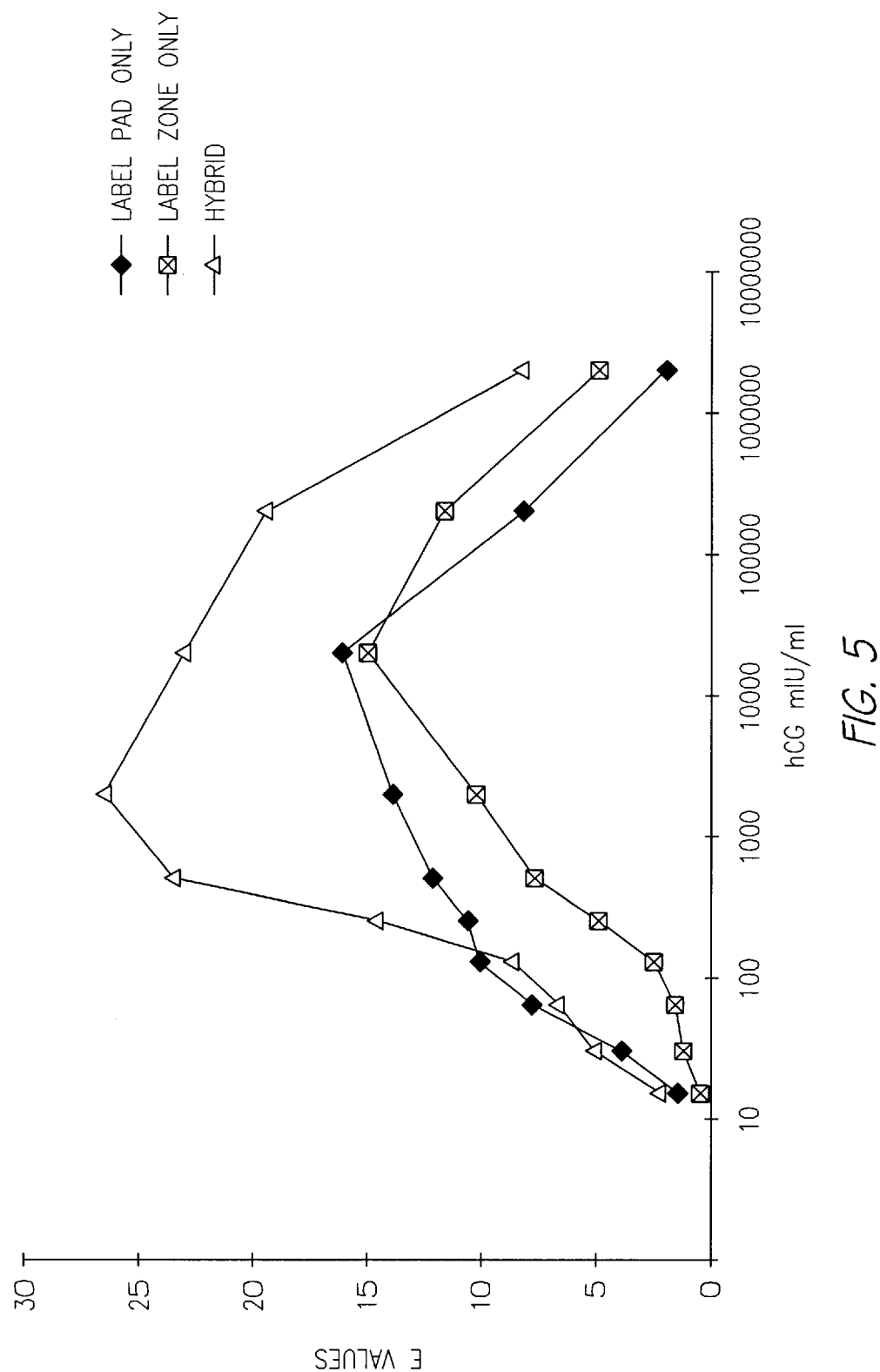
FIG. 5 is a graph showing the intensity obtained at the capture zone at various concentrations of the target analyte for three devices containing different arrangements of the labeling reagent. The reflectance intensity values versus the hCG concentration are shown.

FIG. 4 shows a graph of the intensity at the capture zone vs. the time in minutes. As can be seen from the graph (□—□), placement of the labeling reagent in the discrete zone only results in a quick increase in the concentration of labeling reagent passing the capture zone, followed by a quick decrease. This type of device has a quick clearance time but lower sensitivity—the time for the analyte to bind to the indicator labeling reagent, and the time for the analyte-indicator reagent complex to bind to the capture reagent are shorter—as shown in FIG. 5 (□—□). While the detection of low concentrations of analyte can be improved by increasing the amount of labeling reagent in the discrete zone, this increase also increases the maximum concentration of labeling reagent passing through the capture zone (See FIG. 6), which may increase the occurrence of false positive results (data not shown).

Figure 7:
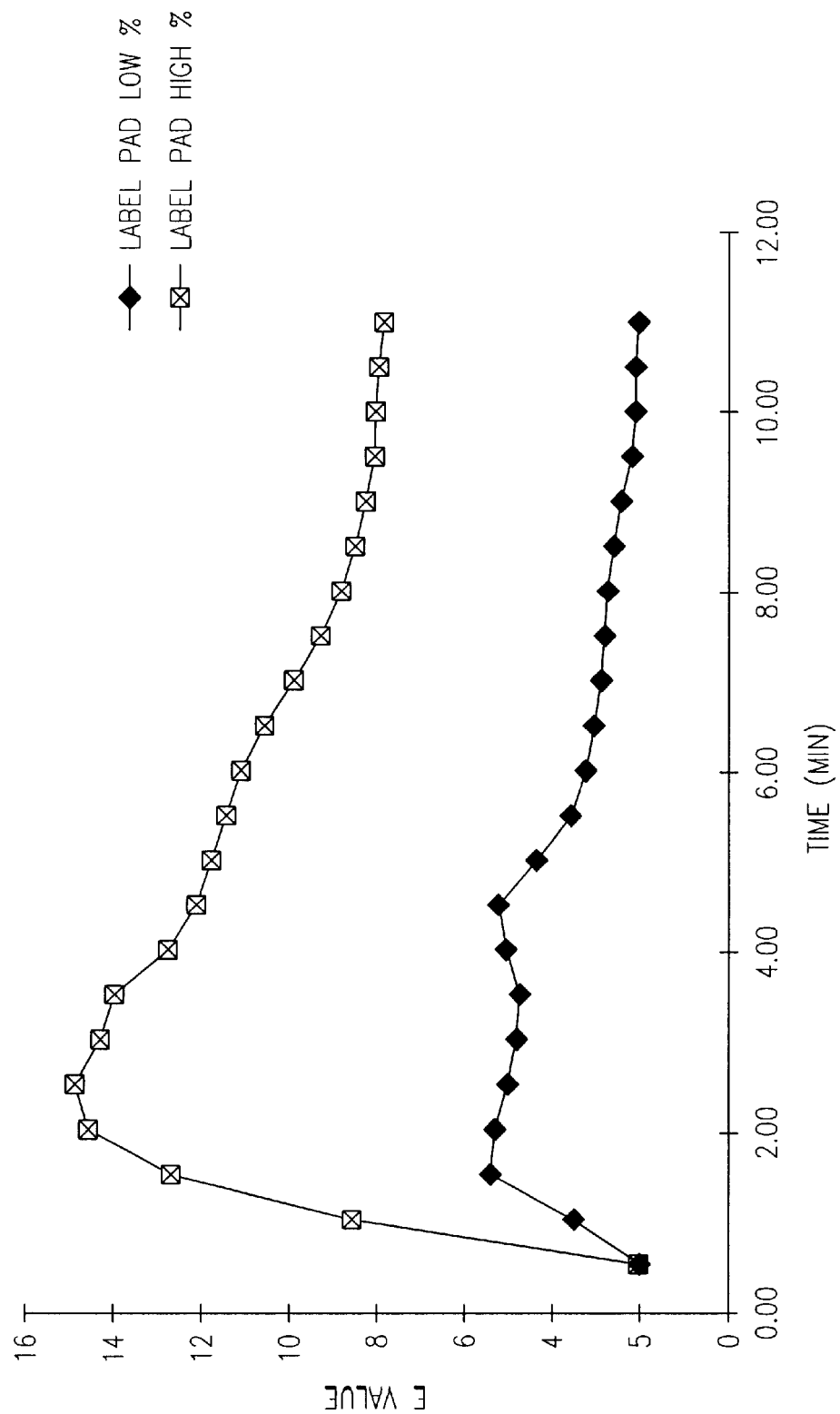
FIG. 7 is a graph showing the intensity of the dye used as a labeling reagent passing through the capture zone over time for high and low percent solids, where the dye has been placed only in the separate labeling reagent region, or label pad.

Alternatively, placement of the labeling reagent in the separate labeling reagent region only (in this example a "label pad"), results in a slow increase in the concentration of labeling reagent passing through the capture zone, followed by a slower trailing decrease in the amount of labeling reagent passing through the capture zone (FIG. 4, ♦—♦). Increasing the amount of labeling reagent in the separate labeling reagent region to increase the amount of labeling reagent which passes the capture zone results in greater clearance times, greater time for the analyte to bind to the indicator labeling reagent, and greater time for the analyte-indicator reagent complex to bind to the capture reagent, which results in sustained release and greater sensitivity (FIG. 7).

Placement of the label in both the label zone and a separate labeling reagent region in the "hybrid" device gives rise to a quick increase in the concentration of the label moving past the capture zone (FIG. 4, ▲—▲). Because the labeling reagent is also placed in a separate labeling reagent region, this high concentration of labeling reagent persists for a longer period than when the labeling reagent is placed in the label zone alone, permitting a longer incubation of the indicator labeling reagent with the analyte and a longer incubation of the analyte-indicator labeling reagent complex with the indicator capture reagent. The total amount of analyte-indicator labeling reagent complex passing through the capture zone is thereby increased, permitting a higher range of sensitivity of the assay device. However, although the range of sensitivity is increased, the maximum level of label passing through the capture zone at any given time point does not exceed the maximum level obtained from placement of the label in the discrete zone only. Therefore, placement of the labeling reagent in both positions increases sensitivity with respect to placing the labeling reagent in a discrete zone without increasing the occurrence of false positive readings. Moreover, the time needed for the concentration of the label to fall to background levels is not significantly increased compared to the device containing the label in the separate labeling reagent region alone. Therefore, clearance time is not adversely affected.

Sensitivity Curve

Samples containing various amounts of target analyte (hCG) were applied to the same three types of assay devices described above, and carried out as described. The intensity of the band formed in the capture zone through binding of the (hCG)-anti-β-hCG antibody-blue latex complex to anti-α-hCG antibody capture reagent was measured at each hCG concentration. The data is shown in Table 2.

TABLE 2

| hCG Concentration (mIU/ml) | Label Pad Only | Label Zone Only | Hybrid |
| --- | --- | --- | --- |
| 15 | 1.54 | 0.51 | 2.36 |
| 30 | 3.98 | 1.23 | 5.2 |
| 62.5 | 7.87 | 1.62 | 6.84 |
| 125 | 10.15 | 2.52 | 8.82 |
| 250 | 10.57 | 4.92 | 14.63 |
| 500 | 12.11 | 7.68 | 23.49 |
| 2000 | 13.81 | 10.2 | 26.51 |
| 20000 | 15.96 | 14.81 | 22.99 |
| 200000 | 8.1 | 11.51 | 19.28 |
| 2000000 | 1.86 | 4.77 | 8.2 |

FIG. 5 shows a graph of the intensity vs. the hCG concentration in mIU/ml.

At low concentrations, the device containing the labeling reagent in a discrete label zone has the lowest sensitivity (FIG. 5, □—□). The "hybrid" device has sensitivity comparable to placement of the indicator reagent in the separate labeling region alone (♦—♦) at concentrations of hCG less than 100 mIU/ml hCG, while the hybrid has the highest sensitivity at concentrations above 100 mIU/ml hCG (▲—▲).

Comparison of High vs. Low % Solids (Labeling Reagent Concentration) in a Separate Labeling Reagent Region (Label Pad) And Comparison of High vs. Low % Solids (Labeling Reagent Concentration) in a Discrete Labeling Zone of the Analyte Detection Region (Label Zone)

Assay strips were assembled as described above with two different concentrations of label in the label pad and two different concentrations of label placed in the discrete zone of the analyte detection region. The low concentrations of label in the label pad and in the label zone are equivalent in total % solids. The high concentrations of the label in the label pad and in the label zone are also equivalent in total solids. The total solids in the high concentration is approximately twice the total solids in the low concentrations. As in the experiments above, assay strips were assembled with label pad only, label zone only, and hybrid (both label pad and label zone). The triplicate strips were run by application of a negative control sample solution to the sample pad. The color development at the capture zone was measured with the CR-241 at 30 second intervals for approximately 10 minutes. E values were recorded for each time interval and are set forth in Table 3.

TABLE 3

| | E Values | | | | |
| --- | --- | --- | --- | --- | --- |
| | Label Zone | | Label Pad | | |
| Time (min) | Low % | High % | Low % | High % | Hybrid |
| 0.50 | 2 | 2 | 2 | 2 | 2 |
| 1.00 | 12.96 | 35.63 | 3.48 | 8.5 | 14.55 |
| 1.50 | 3.99 | 6.11 | 5.42 | 12.63 | 16.92 |
| 2.00 | 3.18 | 4.29 | 5.31 | 14.52 | 15.89 |
| 2.50 | 2.92 | 3.48 | 5 | 14.81 | 13.78 |
| 3.00 | 2.75 | 3.05 | 4.79 | 14.26 | 12.57 |
| 3.50 | 2.54 | 2.78 | 4.72 | 13.91 | 11.58 |
| 4.00 | 2.3 | 2.61 | 5.03 | 12.66 | 10.21 |
| 4.50 | 2.15 | 2.53 | 5.18 | 12.02 | 9.06 |
| 5.00 | 2.09 | 2.47 | 4.29 | 11.68 | 8.57 |
| 5.50 | 2.04 | 2.42 | 3.54 | 11.33 | 8.04 |
| 6.00 | 1.99 | 2.38 | 3.16 | 10.95 | 7.85 |
| 6.50 | 1.97 | 2.32 | 2.93 | 10.42 | 7.71 |
| 7.00 | 1.94 | 2.18 | 2.79 | 9.73 | 7.5 |
| 7.50 | 1.93 | 2.09 | 2.68 | 9.12 | 7.43 |
| 8.00 | 1.93 | 2.01 | 2.62 | 8.68 | |
| 8.50 | 1.91 | 1.98 | 2.45 | 8.36 | |
| 9.00 | 1.9 | 1.92 | 2.32 | 8.11 | |
| 9.50 | 1.91 | 1.8 | 2.05 | 7.92 | |
| 10.00 | 1.9 | 1.9 | 1.98 | 7.88 | |
| 10.50 | 1.89 | 1.75 | 1.97 | 7.79 | |
| 11.00 | 1.88 | 1.77 | 1.88 | 7.68 | |
| 11.50 | 1.88 | 1.75 | | | |
| 12.00 | | | | | |

Figure 6:
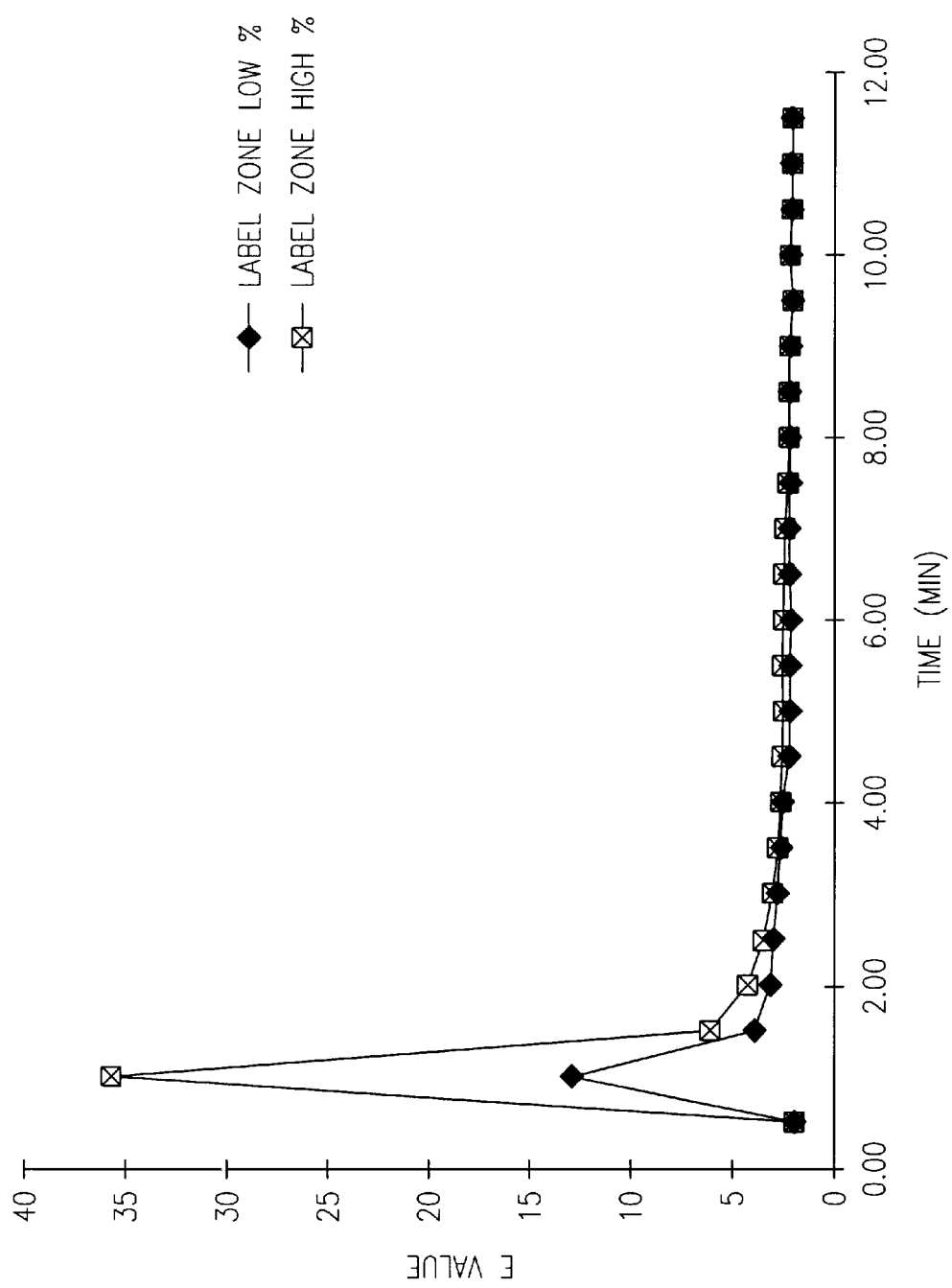
FIG. 6 is a graph showing the intensity of the dye used as a labeling reagent passing through the capture zone over time for high and low percent solids (a measure of the amount of dye present), where the dye has been placed only in the label zone of the analyte detection region.

FIG. 6 shows that the maximum concentration of label passing through the capture zone increases if the amount of the label in the label zone is increased. This may lead to an increase in the number of false positive results. In addition, the time that the analyte-label reagent complex has to react with the capture reagent is not increased.

FIG. 7 shows that both the maximum concentration of label passing through the capture zone and the time that it takes for the label to clear the capture zone is increased if the amount of label in the label is increased. This would give rise to longer assay times and would increase the possibility of false positive results.

Figure 8:
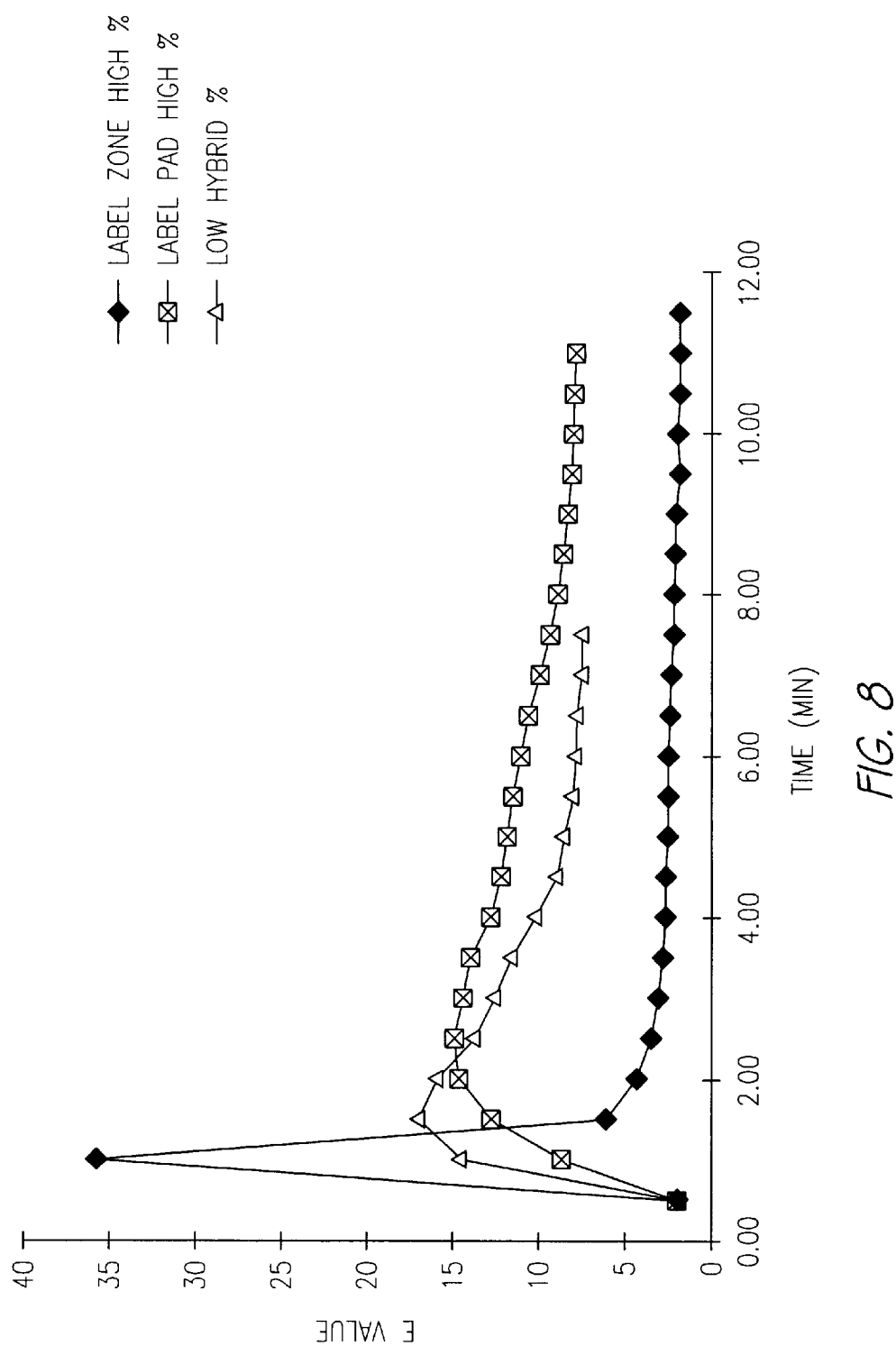
FIG. 8 is an intensity curve graph showing the intensity of the dye used as a labeling reagent passing through the capture zone at various time points for three devices containing different arrangements of the labeling reagent. The same total amount of label was placed in each of the three devices. For two of the devices the dye was placed either in a label pad only or a label zone only. The hybrid device contained the same total amount of label divided between the label pad and the label zone.

FIG. 8 shows the intensity curve where the total label in the hybrid device is approximately the same amount of label contained in the label pad of the device containing high % label in the label pad only, and is also approximately the same amount of label contained in the label pad of the device containing high % in the label zone only.

One skilled in the art will readily appreciate that the present invention is well adapted to carry out the objects and obtain the ends and advantages mentioned as well as those inherent therein. The immunological methods and devices for detecting analytes in biological samples as described herein are presently representative of preferred embodiments, are exemplary and not intended as limitations on the scope of the invention. Changes therein and other uses will occur to those skilled in the art which are encompassed within the spirit of the invention or defined by this scope with the claims.

It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

We claim:

1. An immunochromatographic assay device for detection of the presence or absence of an analyte in a liquid sample, wherein said immunochromatographic assay device comprises:
   (a) a sample receiving region comprising a porous material which conducts lateral flow of a liquid sample, in lateral flow contact with
   (b) an analyte detection region comprising a porous material which conducts lateral flow of said liquid sample, wherein said analyte detection region comprises an immobile indicator capture reagent at a discrete indicator capture reagent situs,
   wherein said immunochromatograplic device also comprises:
      a first indicator labeling reagent zone comprising a first mobile indicator labeling reagent, and a second indicator labeling reagent zone comprising a second mobile indicator labeling reagent wherein the lateral flow characteristics of the indicator labeling reagent in the first zone differ from the lateral flow characteristics of the indicator labeling reagent in the second zone, wherein said first mobile indicator labeling reagent forms a complex binding with said analyte, and wherein said second mobile indicator labeling reagent forms a complex binding with said analyte, and wherein said zones are in lateral flow contact with said sample receiving region and said analyte detection region, and wherein said liquid sample laterally flows from said sample receiving region towards said analyte detection region, and mixes with said first and second indicator labeling reagents to move said first and second indicator labeling reagents towards said analyte detection region, wherein said immobile indicator capture reagent forms a complex comprising said analyte, said first or second mobile indicator labeling reagent and said immobile indicator capture reagent.

2. The device of claim 1 wherein said first mobile indicator labeling reagent in said first indicator labeling reagent zone is mobilized quickly upon lateral flow contact with said sample, and wherein lateral flow contact of said sample with said second mobile indicator labeling reagent in said second labeling reagent zone results in sustained release of said second mobile indicator labeling reagent.

3. The device of claim 1 wherein said second mobile indicator labeling reagent in said second indicator labeling reagent zone is mobilized quickly upon lateral flow contact with said sample, and wherein lateral flow contact of said sample with said first mobile indicator labeling reagent in said first labeling reagent zone results in sustained release of said first mobile indicator labeling reagent.

4. The device of claim 1 wherein said first mobile indicator labeling reagent is located in a separate indicator labeling reagent region, and wherein said second mobile indicator labeling reagent is located in said analyte detection region.

5. An immunochromatographic assay device for detection of the presence or absence of an analyte in a liquid sample, wherein said immunochromatographic assay device comprises:
   (a) a separate sample receiving region comprising a porous material which conducts lateral flow of a liquid sample, wherein said sample receiving region comprises a first mobile indicator labeling reagent at a discrete labeling situs, wherein said first mobile indicator labeling reagent forms a complex binding with said analyte, wherein said sample receiving region is in lateral flow contact with
   (b) a separate analyte detection region comprising a porous material which conducts lateral flow of said liquid sample, wherein said separate analyte detection region comprises a second mobile indicator labeling reagent at a discrete labeling situs, wherein said second mobile indicator labeling reagent forms a complex binding with said analyte, an immobile indicator capture reagent at a discrete capture situs, wherein said immobile indicator capture reagent forms a complex comprising said analyte, said first or second mobile indicator labeling reagent, and said immobile indicator capture reagent, wherein the lateral low characteristics of the first mobile indicator labeling reagent in the sample receiving region differ from the lateral flow characteristics of the second mobile indicator labeling reagent in the analyte detection region wherein said analyte detection region is in lateral flow contact with
   (c) a separate end flow region comprising a porous material which conducts lateral flow of said liquid sample and capable of absorbing excess liquid sample, wherein said liquid sample laterally flows from said sample receiving region towards said end flow region, and mixes with said first and second mobile indicator labeling reagents to move said labeling reagents towards said end flow region.

6. The immunochromatographic assay device of claims 1 or 5 wherein said sample receiving region further comprises a mobile control labeling reagent, and wherein said separate analyte detection region further comprises an immobile control capture reagent at a discrete control situs, and said control capture reagent forms a complex binding said control labeling reagent, and
   wherein said liquid sample further mixes with said control labeling reagent to move said control labeling reagent towards said end flow region.

7. A method to determine the presence or absence of analyte in a sample, which method comprises applying said sample to the sample receiving region of the device of claims 1, 2, 3, 4, 5, or 6 so as to permit said sample to flow through the analyte detection region and into the end flow region, and detecting the presence or absence of analyte in the analyte detection region at the discrete capture reagent situs containing the immobile indicator capture reagent which comprising the analyte, the first or second mobile indicator labeling forms a complex reagent, and the immobile indicator capture reagent.

8. A method to determine the presence or absence of analyte in a sample, which method comprises applying said sample to the sample receiving region of the device of claim 6 so as to permit said sample to flow through the analyte detection region and into the end flow region, and detecting the presence or absence of analyte in the analyte detection region at the discrete capture situs containing the mobile indicator capture reagent, wherein, in the presence of said analyte, said indicator capture reagent forms a complex comprising the analyte, the first or second mobile indicator labeling reagent, and the immobile indicator capture reagent, and detecting the presence or absence of a control signal in the analyte detection region at the discrete control situs containing the control capture reagent capable of binding the control labeling reagent.

9. The method of claim 6 wherein said analyte is human chorionic gonadotropin (hCG).

10. A method to determine the presence or absence of analyte in a sample, which method comprises applying said sample to the sample receiving region of the device of claim 6 so as to permit said sample to flow through the analyte detection region and into the end flow region, and detecting the presence or absence of analyte in the analate detection region at the discrete capture reagent situs containing the immobile indicator capture reagent, wherein, in the presence of said analyte, said immobile indicator capture reagent forms a complex comprising the analyte, the first or second mobile indicator labeling reagent, and the immobile indicator capture reagent, and said first labeling reagent is a monoclonal or polyclonal antibody immunoreactive with a β-epitope of hCG conjugated to blue latex, said second mobile labeling reagent is a monoclonal or polyclonal antibody immunoreactive with a β-epitope of hCG conjugated to blue latex, and said mobile control labeling reagent is BSA conjugated to red latex.

11. The method of claim 8 wherein said capture reagent is a monoclonal or polyclonal antibody immunoreactive with the α-epitope of hCG.

12. The method of claim 9 wherein said control labeling reagent is BSA conjuzated to red latex, and said immobile control capture reagent is a monoclonal or polyclonal antibody immunoreactive with the BSA conjugated to red latex.

13. The method of claim 6 wherein said analyte is streptococcus group A.

14. The method of claim 13 wherein said first indicator labeling reagent is a polyclonal antibody immunoreactive with group A streptococcus conjugated to labeling particle.

15. The method of claim 14 wherein said capture reagent is a polyclonal antibody immunoreactive with group A streptococcus.

* * * * *